(12) United States Patent
Riddleberger

(10) Patent No.: US 12,718,952 B2
(45) Date of Patent: Aug. 25, 2026

(54) TIERED ASSESSMENT FOR IN-HOME SPECIALIZED CARE

(71) Applicant: DispatchHealth Management, LLC, Denver, CO (US)

(72) Inventor: Kevin William Riddleberger, Superior, CO (US)

(73) Assignee: DISPATCHHEALTH MANAGEMENT, LLC, Denver, CO (US)

( * ) Notice: Subject to any disclaimer, the term of this patent is extended or adjusted under 35 U.S.C. 154(b) by 454 days.

(21) Appl. No.: 17/500,825

(22) Filed: Oct. 13, 2021

(65) Prior Publication Data

US 2022/0115141 A1 Apr. 14, 2022

Related U.S. Application Data

(60) Provisional application No. 63/091,147, filed on Oct. 13, 2020.

(51) Int. Cl.
*G16H 50/30* (2018.01)
*G16H 50/20* (2018.01)

(52) U.S. Cl.
CPC ............. *G16H 50/30* (2018.01); *G16H 50/20* (2018.01)

(58) Field of Classification Search
CPC ............................... G16H 50/20; G16H 50/30
USPC .............................................................. 705/3
See application file for complete search history.

(56) References Cited

U.S. PATENT DOCUMENTS

| | | | |
|---|---|---|---|
| 5,122,959 | A | 6/1992 | Nathanson et al. |
| 6,106,459 | A | 8/2000 | Clawson |
| 6,607,481 | B1 | 8/2003 | Clawson |
| 7,249,036 | B2 | 7/2007 | Bayne |

(Continued)

FOREIGN PATENT DOCUMENTS

| | | | |
|---|---|---|---|
| EP | 0875035 | B1 | 6/2002 |
| TW | 201818363 | A | 5/2018 |

(Continued)

OTHER PUBLICATIONS

Dispatchhealth , "How our mobile urgent care works for you", retrieved from: https://www.dispatchhealth.com/how-it-works/ [Downloaded Sep. 26, 2023].

(Continued)

*Primary Examiner* — Hiep V Nguyen
(74) *Attorney, Agent, or Firm* — HOLZER PATEL DRENNAN

(57) ABSTRACT

The tiered assessments disclosed herein are used to aid a health care professional in determining if a patient is eligible for specialized health care (e.g., hospital-level care) delivered in the patient's home. A mobile acute care unit arrives at the patient's home, performs an initial assessment of the patient on-site, and performs the medical services that the mobile acute care unit is capable of in the patient's home. If the patient is in need for further services that the mobile acute care unit cannot provide, the mobile acute care unit could trigger a secondary (or tiered) assessment to aid a health care professional in determining if a specialized mobile care is appropriate for the patient's needs. The secondary assessment includes an evaluation of the patient's home as it relates to the ability of a specialized mobile care unit to render services safely and effectively.

19 Claims, 13 Drawing Sheets

(56) References Cited

U.S. PATENT DOCUMENTS 7,420,472 B2 9/2008 Tran
8,019,622 B2 9/2011 Kaboff et al.
8,117,046 B2 2/2012 Bayne
8,494,868 B2 7/2013 Saalsaa
8,515,777 B1 8/2013 Rajasenan
9,202,253 B2 12/2015 Macoviak et al.
9,208,288 B2 12/2015 Putrino
11,031,124 B2 6/2021 Johnson et al.
11,127,502 B2 9/2021 Villazón-Terrazas et al.
2003/0137426 A1 7/2003 Anthony et al.
2003/0171954 A1 9/2003 Guerin et al.
2005/0131740 A1 6/2005 Arnold et al.
2005/0234740 A1 10/2005 Krishnan et al.
2005/0234742 A1 10/2005 Hodgdon
2006/0084847 A1* 4/2006 Reed .................... G06F 15/173 600/595
2006/0173708 A1 8/2006 Vining et al.
2008/0058615 A1 3/2008 Clapp et al.
2008/0076971 A1 3/2008 Clapp
2008/0262867 A1 10/2008 Bayne et al.
2009/0019552 A1 1/2009 Mclaughlin et al.
2009/0099862 A1 4/2009 Fireman et al.
2010/0305966 A1 12/2010 Coulter et al.
2011/0105853 A1 5/2011 Rakowski et al.
2012/0046965 A1 2/2012 Ryan et al.
2013/0095459 A1* 4/2013 Tran ...................... G09B 19/00 434/247
2013/0151272 A1 6/2013 Vis
2013/0304511 A1 11/2013 Gunter
2014/0214439 A1 7/2014 Young et al.
2014/0214441 A1* 7/2014 Young ................... G16H 10/20 705/2
2014/0316797 A1 10/2014 Biernacki et al.
2015/0106123 A1 4/2015 Amarasingham et al.
2015/0187018 A1 7/2015 Knaust et al.
2015/0213225 A1 7/2015 Amarasingham et al.
2015/0242769 A1 8/2015 Kezeu
2015/0278732 A1 10/2015 Fiedler et al.
2016/0125158 A1 5/2016 Erdmann et al.
2016/0165189 A1* 6/2016 Walker ................... G16Z 99/00 348/143
2016/0188834 A1 6/2016 Erdmann et al.
2016/0192312 A1 6/2016 Lambert et al.
2016/0196389 A1 7/2016 Moturu et al.
2016/0253464 A1 9/2016 Balwani et al.
2017/0011193 A1 1/2017 Arshad et al.
2017/0076048 A1* 3/2017 Bayne ................... G16H 50/20
2017/0161433 A1 6/2017 Perretta
2017/0177801 A1 6/2017 Ryan et al.
2018/0121619 A1 5/2018 Perlroth et al.
2018/0308584 A1 10/2018 Prather et al.
2019/0115097 A1 4/2019 Macoviak et al.
2019/0197438 A1 6/2019 Meredith et al.
2019/0290214 A1 9/2019 Ci
2019/0311790 A1 10/2019 Dadkhahnikoo et al.
2019/0311799 A1 10/2019 Watson et al.
2020/0004583 A1 1/2020 Kelly et al.
2020/0100724 A1 4/2020 Golay
2020/0181710 A1 6/2020 Steelman
2020/0293712 A1 9/2020 Potts et al.
2021/0098090 A1 4/2021 Thomas et al.
2021/0193302 A1 6/2021 Day et al.
2021/0217529 A1 7/2021 Myers et al.

FOREIGN PATENT DOCUMENTS

WO WO-2015157576 A1 * 10/2015 ............ G16H 10/60
WO 2016010649 A1 1/2016
WO 2017012108 A1 1/2017

OTHER PUBLICATIONS

Dispatchhealth , “We’re ready to treat you in the comfort of home”, retrieved from: https://www.dispatchhealth.com/what-we-treat/ [downloaded Sep. 26, 2023].

Urgentcare2go , “Watch Our Short Video to Learn Exactly How it Works”, retrieved from: https://urgentcare2go.com/Home/HowItWorks [downloaded Sep. 26, 2023].

* cited by examiner

MARKET:
80027-DEN

ON-BOARDING PATIENT:
Francisco Milner
302

911 CARE REQUEST
304

Case Notes
Start typing to add a note...
316

MARKET 318

SCHEDULING 320

DEMOGRAPHICS 322

CASE DETAILS

CHANNEL 326

LOCATION 328

ATHENA PATIENT 330

INSURANCE 332

BILLING 334

CARE PLAN 336

PROVIDERS 338

50% completed 340

ORIGIN PHONE NUMBER
111-222-3333 306

ACTIVATED BY 308
- Patient
- Patient 's Family
- Facility Staff
- Patient's Clinician
- Home health team
- Bystander
- Patient's Co-worker
- Other POWER OF ATTORNEY 310
Does the patient make their own medical decisions?
- Yes
- No CHIEF COMPLAINT 312
Provide a brief description
n/v

RISK STRATIFICATION 314

Select Recommended Protocol

| Screening Protocol | Base Risk Score |
| --- | --- |
| Nausea/Vomiting | 1 |
| General Complaint | 1 |
| Post-acute Patient | 1 |
| DispatchHealth Acute Care - follow up visit | 0 |

FIG. 3

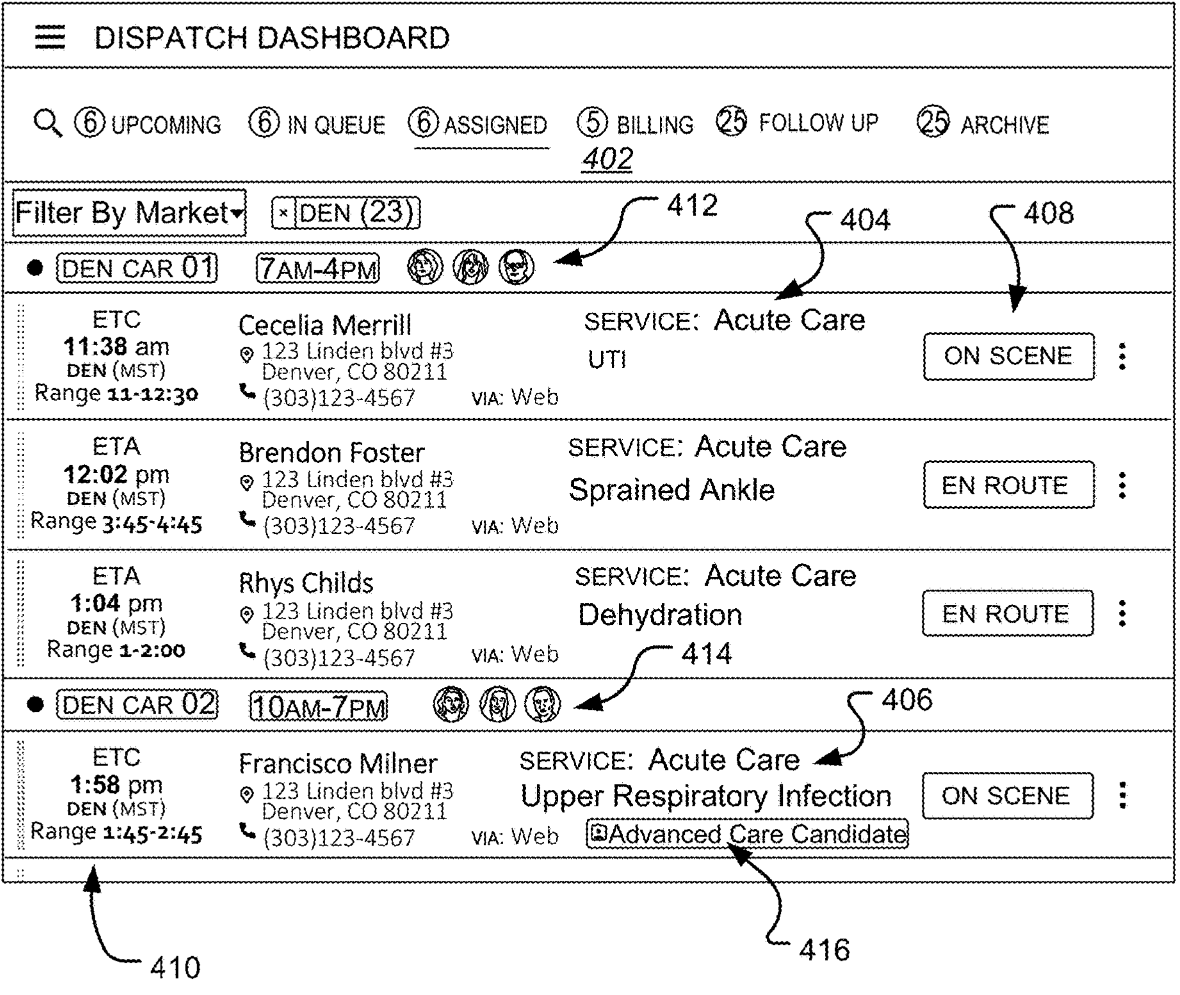
FIG. 4

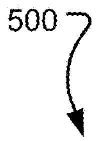
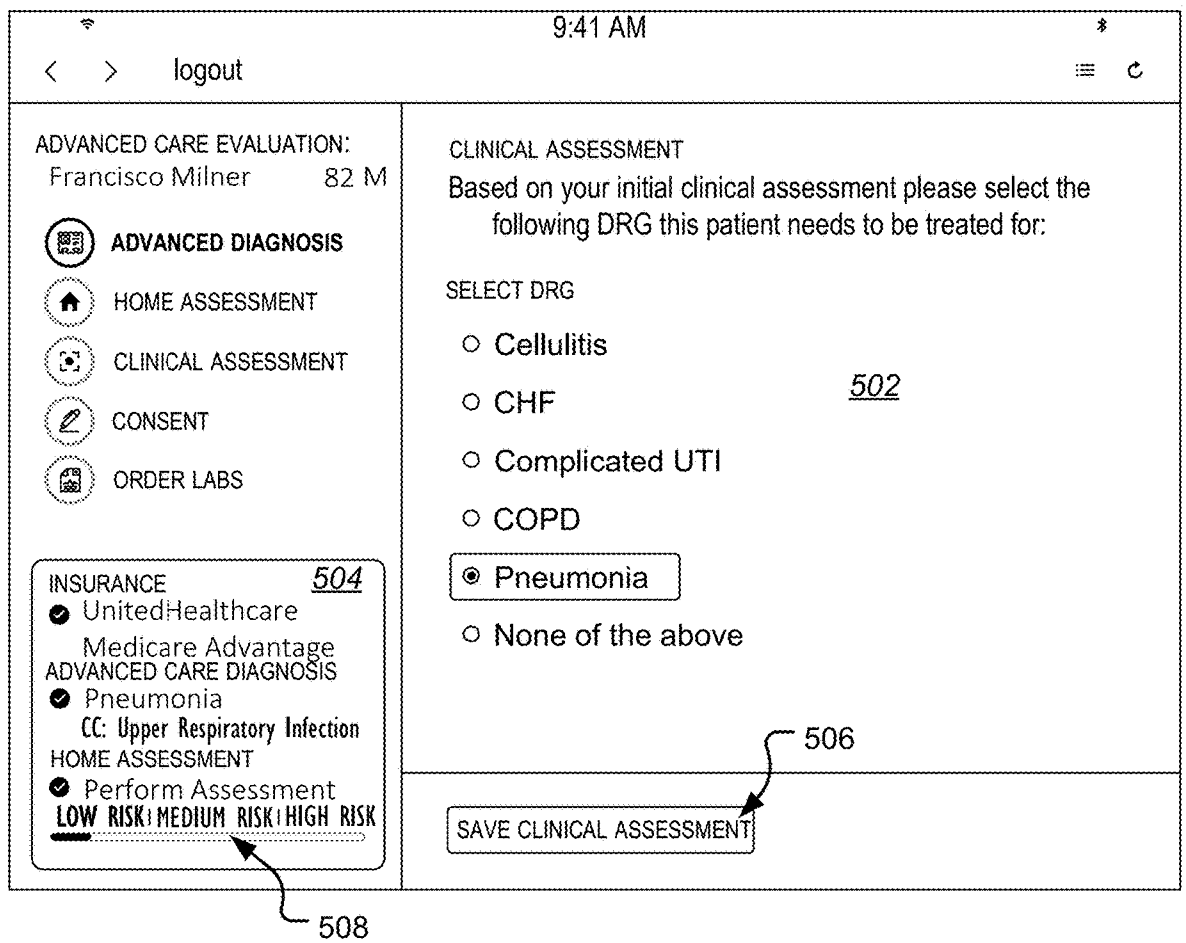
FIG. 5

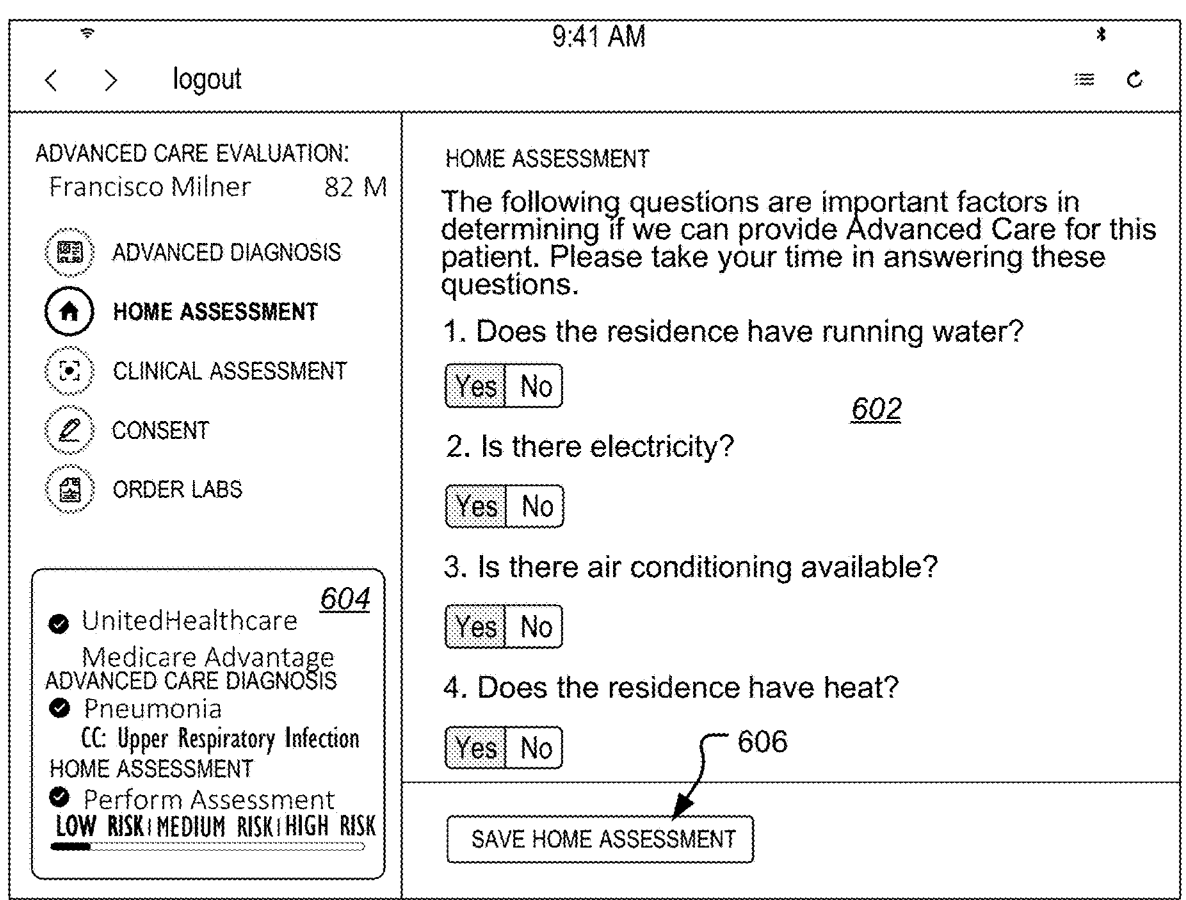
FIG. 6

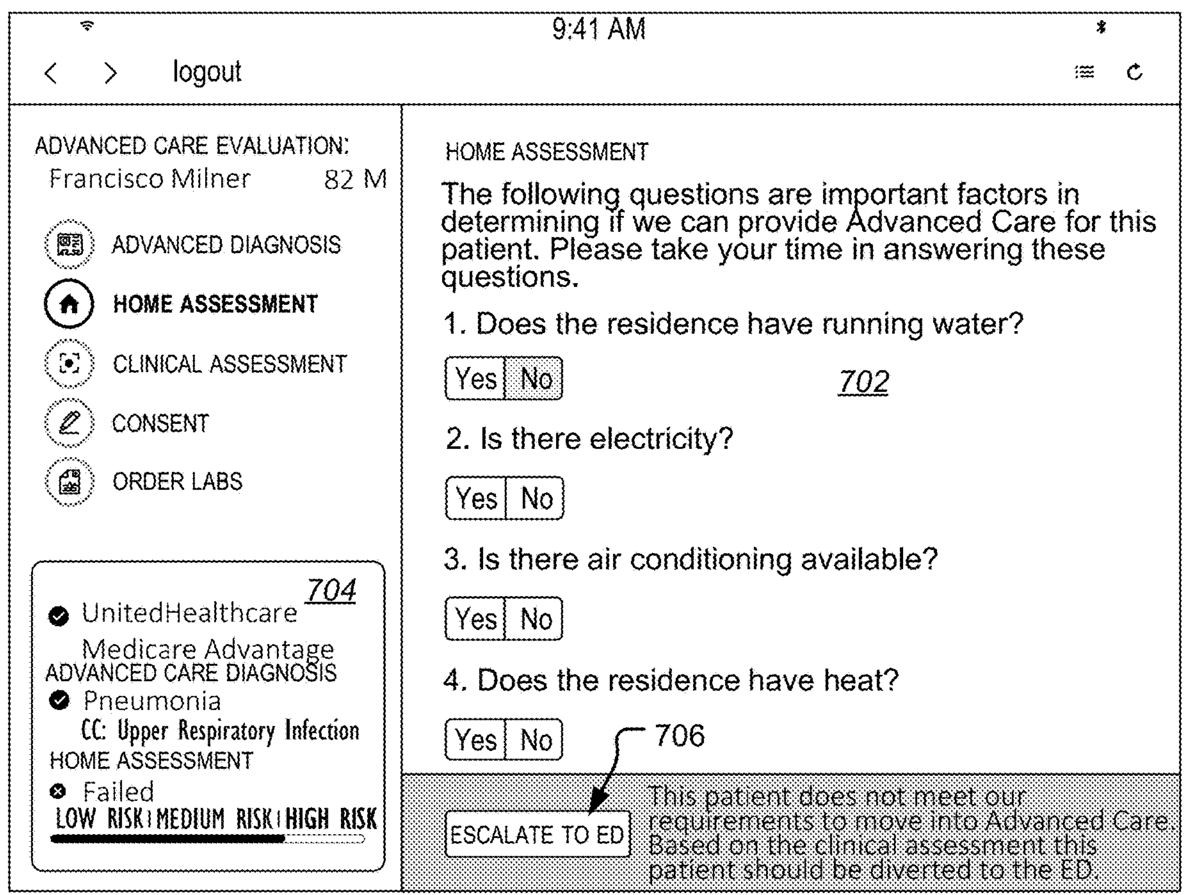
FIG. 7

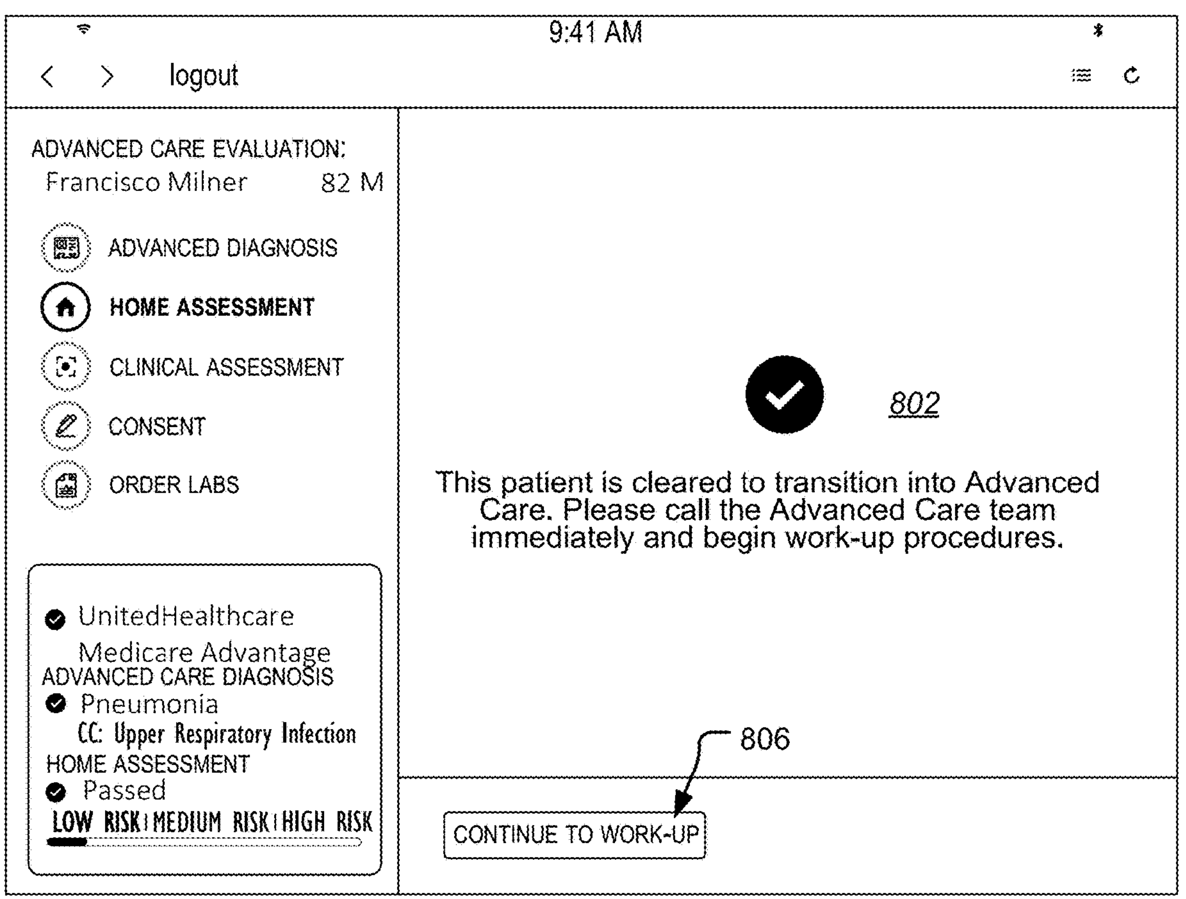
FIG. 8

9:41 AM logout

ADVANCED CARE EVALUATION:
Francisco Milner 82 M

ADVANCED DIAGNOSIS
HOME ASSESSMENT
CLINICAL ASSESSMENT
CONSENT
ORDER LABS

UnitedHealthcare
Medicare Advantage
ADVANCED CARE DIAGNOSIS
Pneumonia
CC: Upper Respiratory Infection
HOME ASSESSMENT
Passed
LOW RISK | MEDIUM RISK | HIGH RISK

ADVANCED CARE WORK-UP

Please complete the following work-up items

LABS

- ☐ CBC
- ☐ BMP

IMAGING

- ☐ Chest X-Ray

902

OTHER INCLUSION CRITERIA

- ☐ Meets Clinical Diagnosis of Pneumonia
- ☐ Peripheral O2 sat <92 percent on RA (or a significant change from baseline)
- ☐ PSI scores of ≥III and CURB-65 scores ≥1 (or CURB-65 score ≥2 if age >65
- ☐ Complicating factor making routine ambulatory PNA treatment unsafe or not feasible (i.e., inability to take oral medications, cognitive or functional impairment, etc.)

TRANSITION TO ADVANCED CARE

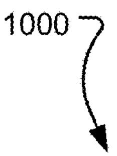
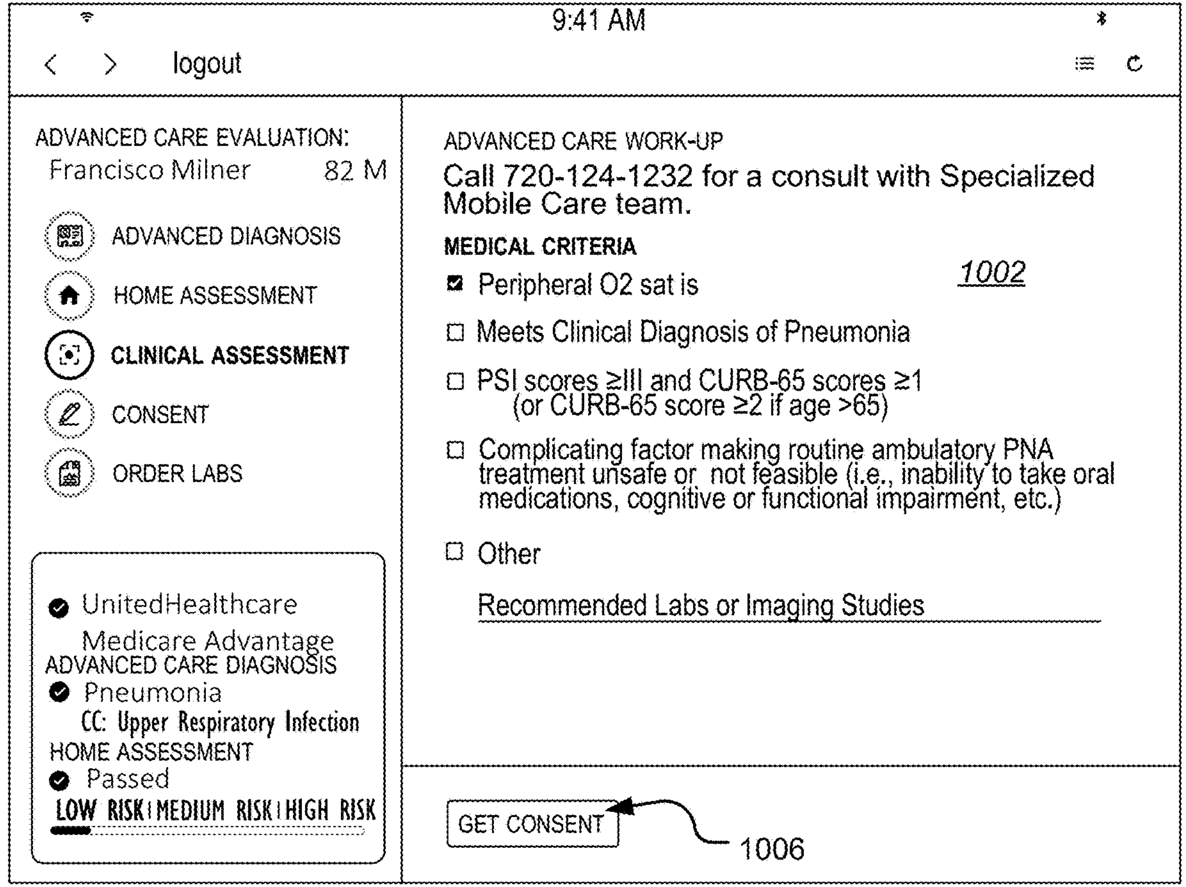
FIG. 10

1200

Perform an acute care service on a patient in the patient's home.
1205

Perform a threshold evaluation to determine patient eligibility for a specialized health care service.
1210

Collect the threshold evaluation results.
1215

Perform an environmental assessment of the patient's home.
1220

Collect the environmental assessment results.
1225

Perform a clinical assessment of the patient.
1230

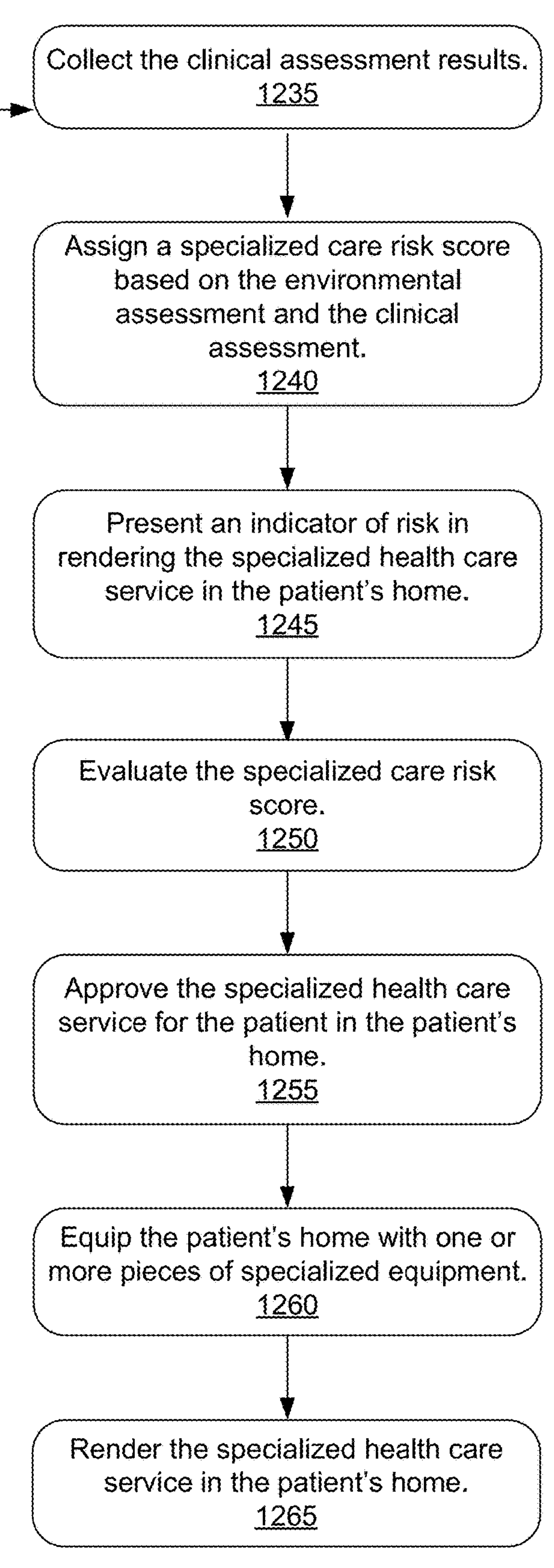

FIG. 12

TIERED ASSESSMENT FOR IN-HOME SPECIALIZED CARE

CROSS-REFERENCE TO RELATED APPLICATIONS

The present application claims benefit of priority to U.S. Provisional Patent Application No. 63/091,147, entitled "Tiered Assessment for In-Home Hospital Care" and filed on Oct. 13, 2020, which is specifically incorporated by reference herein for all that it discloses or teaches.

BACKGROUND

Acute care is a branch of secondary health care where a patient receives active but short-term treatment for a severe injury, severe illness, or other urgent medical condition. Acute care services are generally delivered by teams of health care professionals from a range of medical and surgical specialties. Acute care traditionally requires a stay in a hospital emergency department and in-patient facility, ambulatory surgery center, urgent care center, or other short-term stay facility, along with the assistance of diagnostic services, surgery, or follow-up outpatient care in the community.

A patient's entry into the acute care system is often under-informed or mis-informed, resulting in the patient procuring services that are not appropriate for the patient's actual needs. More specifically, the patient may procure services that exceed that patient's actual needs, resulting in increased cost of treatment. Alternatively, the individual may procure services that are insufficient for the patient's actual needs, resulting in a transfer to a different service provider. This delays treatment for the patient and increases the associated cost of treating the patient overall.

Further, some patients' injury or illness may be sufficiently severe and/or urgent that the patient's only existing option is admission to a specialized care facility (e.g., a hospital emergency department, a stand-alone emergency facility, or a skilled nursing facility (SNF)) for treatment. However, some of these patients could be treated within their home, if their home environment is appropriate for treating the patients' injury or illness and is properly equipped with the appropriate personnel and equipment.

Systems and methods for providing right-sized acute care services can decrease cost and time-to-treatment, while maintaining quality of service for individual patients. Further, systems and methods for providing in-home care in place of specialized care facilities, can further decrease cost and generally improve patient mental well-being.

SUMMARY

Implementations described and claimed herein address the foregoing problems by providing specialized mobile health care services to a patient in the patient's home. The method comprises performing a threshold evaluation to determine patient eligibility for a specialized health care service to be rendered in the patient's home, performing an environmental assessment of the patient's home at the patient's home, the environmental assessment including both patient-focused safety factors and provider-focused safety factors, performing a clinical assessment of the patient, evaluating a specialized care risk score based on the environmental assessment and the clinical assessment, the specialized care risk score attributable to providing the specialized health care service in the patient's home, and rendering the specialized health care service in the patient's home.

Implementations described and claimed herein address the foregoing problems by further providing one or more tangible computer-readable storage media encoding computer-executable instructions for executing on a computer system a computer process for providing specialized mobile health care services to a patient in the patient's home. The computer process comprises collecting a threshold evaluation to determine patient eligibility for a specialized health care service to be rendered in the patient's home, collecting an environmental assessment of the patient's home at the patient's home, the environmental assessment including both patient-focused safety factors and provider-focused safety factors, collecting a clinical assessment of the patient, assigning a specialized care risk score based on the environmental assessment and the clinical assessment, the specialized care risk score attributable to risk in providing the specialized health care service in the patient's home, and presenting an indicator of risk in rendering the specialized health care service in the patient's home.

Implementations described and claimed herein address the foregoing problems by still further providing tiered mobile health care services to a patient. The method comprises performing an acute care service on the patient in the patient's home by a health care professional member of a mobile acute care unit on-site at the patient's home, performing a threshold evaluation to determine patient eligibility for a specialized health care service to be rendered in the patient's home, performing an environmental assessment of the patient's home by the health care professional, the environmental assessment including both patient-focused safety factors and provider-focused safety factors, performing a clinical assessment of the patient by the health care professional, approving a specialized health care service for the patient in the patient's home by the health care professional, the health care professional evaluating a specialized care risk score based on the environmental assessment and the clinical assessment, the specialized care risk score attributable to providing the specialized health care service in the patient's home, the health care professional further conferring with another health care professional associated with the specialized health care service, and rendering the specialized health care service in the patient's home using a specialized mobile care unit.

Other implementations are also described and recited herein.

BRIEF DESCRIPTIONS OF THE DRAWINGS

FIG. 3 illustrates an example patient on-boarding user interface for a predictive analytics tool (also referred to herein as a first stage of a tiered assessment) to right-size the patient's access to acute care services.

FIG. 4 illustrates an example dashboard of assigned acute care patients for a specific market.

FIG. 5 illustrates an example dashboard for an ADVANCED CARE DIAGNOSIS portion of an ADVANCED CARE EVALUATION of a patient.

FIG. 6 illustrates an example dashboard for a HOME ASSESSMENT portion of an ADVANCED CARE EVALUATION of a patient.

FIG. 7 illustrates another example dashboard for a HOME ASSESSMENT portion of an ADVANCED CARE EVALUATION of a patient.

FIG. 8 illustrates confirmation screen 800 for completion of a HOME ASSESSMENT portion of an ADVANCED CARE EVALUATION of a patient.

FIG. 9 illustrates an example dashboard for a first page of a CLINICAL ASSESSMENT portion of an ADVANCED CARE EVALUATION of a patient.

FIG. 10 illustrates an example dashboard 1000 for a second page of the CLINICAL ASSESSMENT portion of an ADVANCED CARE EVALUATION of a patient.

FIG. 12 illustrates further example operations for providing right-sized medical care to a patient.

DETAILED DESCRIPTIONS

Figure 1:
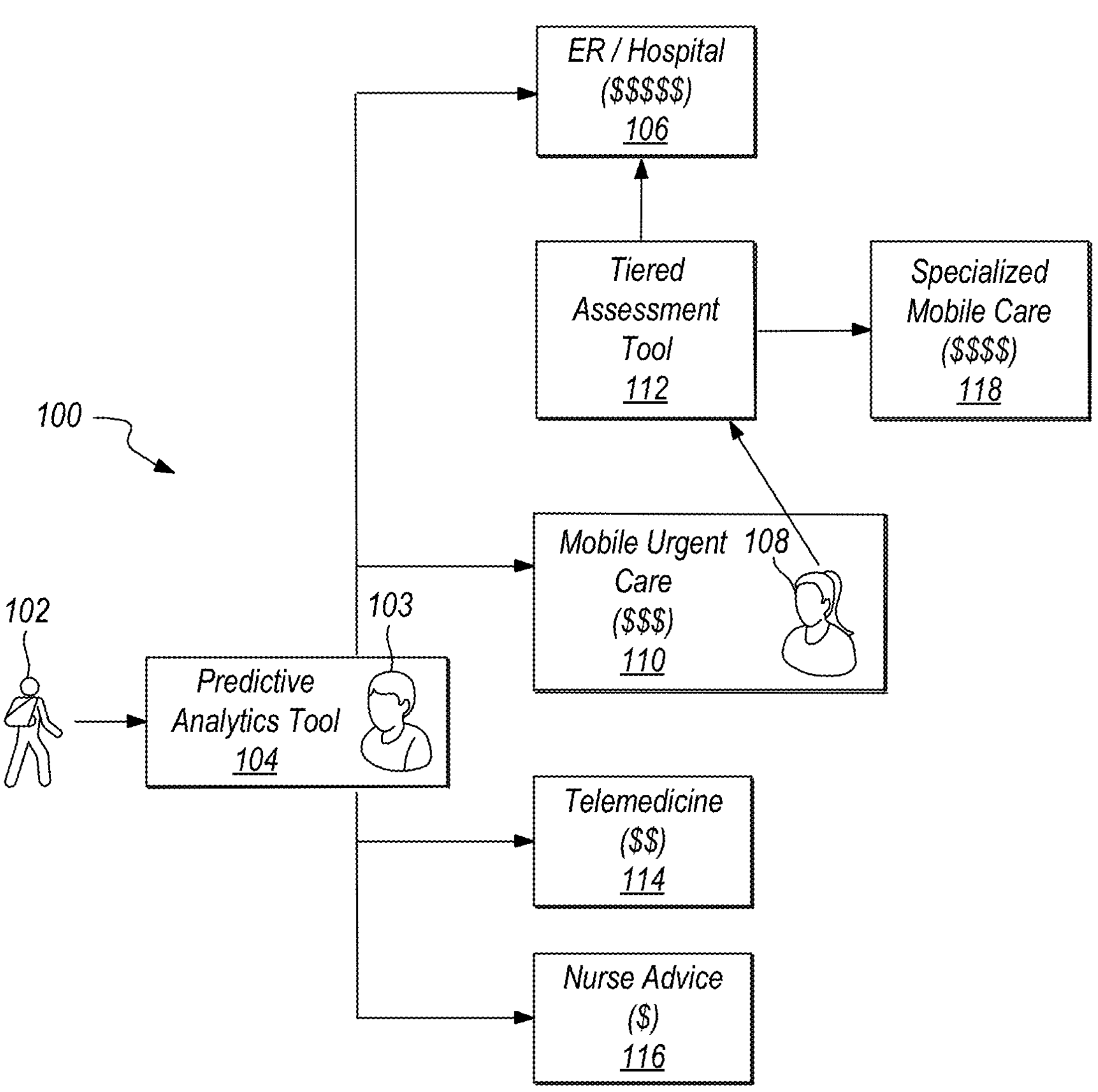
FIG. 1 illustrates a first example flowchart illustrating a patient using a personalized predictive analytics tool and tiered assessment tool to right-size the patient's access to health care services.

The presently disclosed technology provides an integrated and convenient tiered assessment and care solution that extends the capabilities of a patient's health care team.

The patient may choose from a number of options to procure acute care when presented with an injury, illness, or other urgent medical condition based on the patient's perceived needs, which may differ from the patient's actual needs. For example, the patient may call 911 to request ambulatory services, visit an emergency room (ER), visit an urgent care center, visit the patient's primary care physician's office (PCP), or call a nurse advice hotline to procure acute care. The patient's choice in selecting acute care is often under-informed and/or mis-informed (e.g., a selection is based on the patient's prior experience, prior experience (s) of a close friend or family member, results of the patient's Internet research, etc.).

For example, when a patient calls 911 and requests ambulatory services, the patient is automatically transported to an ER for treatment. No option is available for diverting the patient to a different, lower cost acute care service if ER services are not warranted for the patient's actual needs. Similarly, if the patient directly accesses an ER for treatment, the ER will diagnose and provide treatment, if needed. Any diversion of the patient to a different acute care service is subsequent to the patient's initial treatment or diagnosis at the ER, which adds cost and may delay the patient's treatment if the patient is ultimately diverted to a different acute care service.

In another example, when a patient visits an urgent care center or PCP, the patient is initially diagnosed and treated on-site. If the urgent care center or PCP does not have sufficient capability to treat the patient, the patient is referred to the ER or other acute care service. Further, some urgent care centers and PCPs lack sufficient staffing and advanced treatment capability to make any referral other than to the ER. The patient's access to the ER or other acute care service via the urgent care center or PCP may delay treatment for the patient and increase overall cost as compared to the patient accessing a right-sized acute care service directly. Further, if the patient could be sufficiently treated at the patient's PCP, but was instead treated elsewhere, treatment feedback to the patient's PCP is often inadequate or non-existent.

In still another example, the patient may call a nurse advice hotline in an attempt to right-size their acute care service. However, the information the patient provides the nurse may be incomplete, the nurse may not have access to the patient's prior healthcare data, and the nurse does not have the ability to do any physical diagnosis or triage. In order to limit liability and due to potential use of the nurse hotline as a marketing tool, many patients may be directed to the ER when a more right-sized treatment alternative may be available.

Some prior art solutions provide a mobile acute care unit adapted to deliver the services of an urgent care center or PCP in the patient's home in an effort to right-size treatment of the patient's medical condition. When a patient receives a visit from a mobile acute care unit, the patient is initially diagnosed and treated in their home. However, if the mobile acute care unit does not have sufficient capability to treat the patient, the patient is referred to the ER or other higher or different level acute care service. The tiered assessments disclosed herein identify a subset of patients that cannot be treated by the mobile acute care unit but could be safely treated by a specialized mobile health care service within the patient's home and without admission to a specialized care facility (e.g., an emergency room). A substantial time and cost savings and resulting performance advantage may be obtained by right-sizing treatment of the patient's medical condition based on a tiered assessment at the patient's first point of entry into an acute care system.

The tiered assessments disclosed herein are used to aid a health care professional in determining if a patient is eligible for a specialized mobile care unit to deliver specialized health care (e.g., hospital-level care) delivered in the patient's home. In various implementations, the specialized mobile care unit may have capabilities specific to the patient's needs and different from that of a mobile acute care unit, which is also described herein. In an example implementation, the mobile acute care unit arrives at the patient's home, performs an initial assessment of the patient on-site, and performs the medical services that the mobile acute care unit is capable of in the patient's home. If the patient is in need for further services that the mobile acute care unit cannot provide based on the acuity of the patient, the mobile acute care unit could perform a secondary (or tiered) assessment to aid a health care professional in determining if a specialized mobile care (e.g., in-home hospitalization) is appropriate for the patient's needs.

The secondary assessment (also referred to herein as an environmental assessment or an environments/social assessment) includes an evaluation of the patient's home as it relates to the patient's health and safety (patient-focused safety factors), as well as potential risks to health and safety of health care professionals that would render care in the patient's home (provider-focused safety factors). More specifically, the secondary assessment includes an evaluation of the patient's home as it relates to the ability of a specialized mobile care unit to render services safely and effectively. This may include assessing the availability of running water, electricity, state of cleanliness, patient ability to ambulate within the home, presence of stairs to access bedroom(s), presence of guns or other weapons that might endanger health care professionals, as examples. This is distinct from an initial assessment that is mostly focused on whether a mobile acute care unit can render services based on the patient's condition and illness/injury.

In summary, the first assessment (acute care assessment) is directed at patient's condition and viability of treating the patient in their home. The secondary assessment (environmental assessment or an environments/social assessment) adds a component directed to the patient's environment (e.g., their home) being adequate to enable the specialized mobile care unit render services as well as the environment being adequate to ensure the health and safety of the patient and health care professionals. The secondary assessment will also add a component that is specific to the patient's illness/injury to determine if the patient acuity level meets standards in place to hospitalize the patient in their home.

In various implementations, the specialized mobile care unit may perform the same or similar clinical services as a hospital. The specialized mobile care unit may have hospitalist training and the treatment rendered may be referred to herein as "in-home hospitalization." In addition to hospitalist trained personnel, the specialized mobile care unit personnel may have training specific to the needs of the patient. Still further, the specialized mobile care unit may carry equipment specific to the needs of the patient (e.g., a medical grade bed, imaging equipment, personal emergency response system (PERS), a medical data link over the Internet, portable oxygen, and remote patient monitoring technology devices, etc.). The secondary (tiered) assessment may be used to determine a patient's eligibility for in-home hospitalization.

In other implementations, the specialized mobile care unit may perform specialized services that are outside of that typically available at a hospital, such as that of a skilled nursing facility (SNF) providing long-term nursing care. The specialized mobile care unit may have SNF-specific training and equipment and the treatment rendered may be referred to herein as "in-home SNF." The secondary (tiered) assessment may be used to determine a patient's eligibility for in-home SNF.

FIG. 1 illustrates a first example flowchart 100 illustrating a patient 102 using a predictive analytics tool 104 and a tiered assessment tool 112 to right size the patient's access to health care services. The patient 102 accesses the tool 104 via a web-based interface (e.g., via a personal computer, a tablet, a smartphone, a wearable-device, etc.), a telephone-based interface (e.g., via a public switched telephone network ("PSTN"), a wireless network, a private branch exchange ("PBX"), etc.), or a combination interface (e.g., Voice over IP ("VoIP")), which links the patient 102 to the tool 104. In various implementations, a representative for the patient 102 (e.g., the patient's medical doctor (MD), a friend, and/or an employer) may access the tool 104 on behalf of the patient 102. The tool 104 may also utilize a human representative 103 to query the patient (or MD, friend, or employer) and input relevant data into the tool 104 on behalf of the patient 102. The human representative 103 may also be a health care professional tasked with using the tool 104 to help the patient 102 evaluate their options for obtaining health care services.

The patient 102 enters identifying information and a description of the injury and/or symptoms into the tool 104. The tool 104 uses a combination of the patient's actual medical history (e.g., pulled from a health information exchange ("HIE"), such as the Colorado Regional Health Information Organization ("CORHIO"), or other medical databases), the patient's demographics (e.g., age, sex, physical location), and the patient's description of the injury and/or symptom to risk-stratify the patient's complaint and generate a risk score to aid the patient 102 in selecting an appropriate acute care service. In implementations that include a wearable device, a camera, or other data-collecting device (not shown), the tool 104 may collect non-invasive biometric data from the patient 102 (e.g., pulse, blood pressure, imagery of an injury, etc.) for use in generating the risk score for the patient 102. The patient's care options are described below and depicted in FIG. 1 in descending order of relative cost (also indicated by a number of "$" signs).

If the patient's risk score is particularly high (e.g., a score of 2.5-3.0 or "red"), the patient 102 may call 911 for ambulatory service to an ER or otherwise travel to the ER immediately (ER/Hospital ($$$$$) 106). While ER acute care services are typically the most expensive, if the patient's risk score is high enough, the expense is well worth it to gain access to ambulatory or ER medical personnel as soon as possible.

If the patient's risk score is moderate (e.g., a score of 1.5-2.49 or "yellow"), the patient 102 may safely procure a lower cost acute care service. For example, the patient 102 may call a mobile urgent acute care unit (Mobile Urgent Care Unit ($$$) 110) that can at least diagnose the patient's illness or injury onsite (without transporting the patient 102 to an ER or calling an ambulatory service), and in some cases treat the patient's illness or injury onsite. Alternatively, the patient 102 may procure a telemedicine care service $ 114 that can remotely diagnose the patient's illness or injury (without transporting the patient 102 to the ER) and in some cases diagnose treat the patient's illness or injury remotely. Telemedicine care service $ 114 can give the patient 102 access to a large network of medical personnel physically located all over the world.

If the patient's risk score is low (e.g., 0-1.49 or "green"), the patient 102 may safely procure an even lower cost acute care service. For example, the patient 102 may call a nurse advice line (or care coordination service) ($) 116 for guidance in treating the patient's illness or injury. More specifically, a nurse may review the output from the tool 104, discuss the illness or injury with the patient 102, and offer recommendations for self-treatment or other treatment of the patient's illness or injury outside of the acute care system (e.g., scheduling an appointment with the patient's PCP).

In some implementations, the patient receives a visit from the Mobile Urgent Care ($$$) 110 as described above, but the Mobile Urgent Care ($$$) 110 is not able to provide the care required by the patient within an acceptable risk tolerance. In prior art solutions, this would likely lead to the patient visiting the ER/Hospital ($$$$$) 106 to receive the appropriate level of care. If a health care professional 108 rendering the Mobile Urgent Care $$ 110 believes that the patient is capable of being treated safely within their home using additional or different resources, the Mobile Urgent Care ($$$) 110 may trigger the tiered assessment tool 112, which is used to provide an analysis above and beyond that of the predictive analytics tool 104 to further assess the patient, their home, and the capabilities of one or more available specialized mobile care units (e.g., Specialized Mobile Care ($$$$) 118). The tiered assessment tool 112 is used to determine if Specialized Mobile Care ($$$$)118 is appropriate for the patient within an acceptable level of risk. If so, the Specialized Mobile Care ($$$$)118 may be dispatched to render the appropriate level of care to the patient within the patient's home.

While the Specialized Mobile Care ($$$$) 118 may be more expensive than the Mobile Urgent Care $$ 110, it is less expensive than the ER/Hospital ($$$$$)" 106. Further, the patient may be happier with the Specialized Mobile Care ($$$$) 118 as it is rendered in the patient's home without visiting the hospital for an in-patient stay. In some implementations, the Specialized Mobile Care ($$$$) 118 is capable of services equivalent to much of which offered at an emergency room and/or hospital (i.e., hospital-level care). In other implementations, the Specialized Mobile Care ($$$$) 118 is capable of services equivalent to much of which offered at a skilled nursing facility (SNF) (i.e., SNF-level care). In still further implementations, the Specialized Mobile Care ($$$$) 118 is capable of services beyond that of the Mobile Urgent Care ($$$) 110, but not equivalent to that available at another specific health care facility.

Sequential use of the predictive analytics tool 104 and then the tiered assessment tool 112 to assess the patient, their home, and the capabilities of one or more available specialized mobile care units is described collectively as tiered assessment of the patient 102 herein. In other implementations, the tools 104, 112 may offer additional health care service options to the patient 102 and provide additional risk score categories. The tools 112, 104 may also be connected to the patient's health insurance as a mechanism to pre-approve a certain level of health care service for the patient's illness or injury to be covered by the patient's health insurance.

Figure 2:
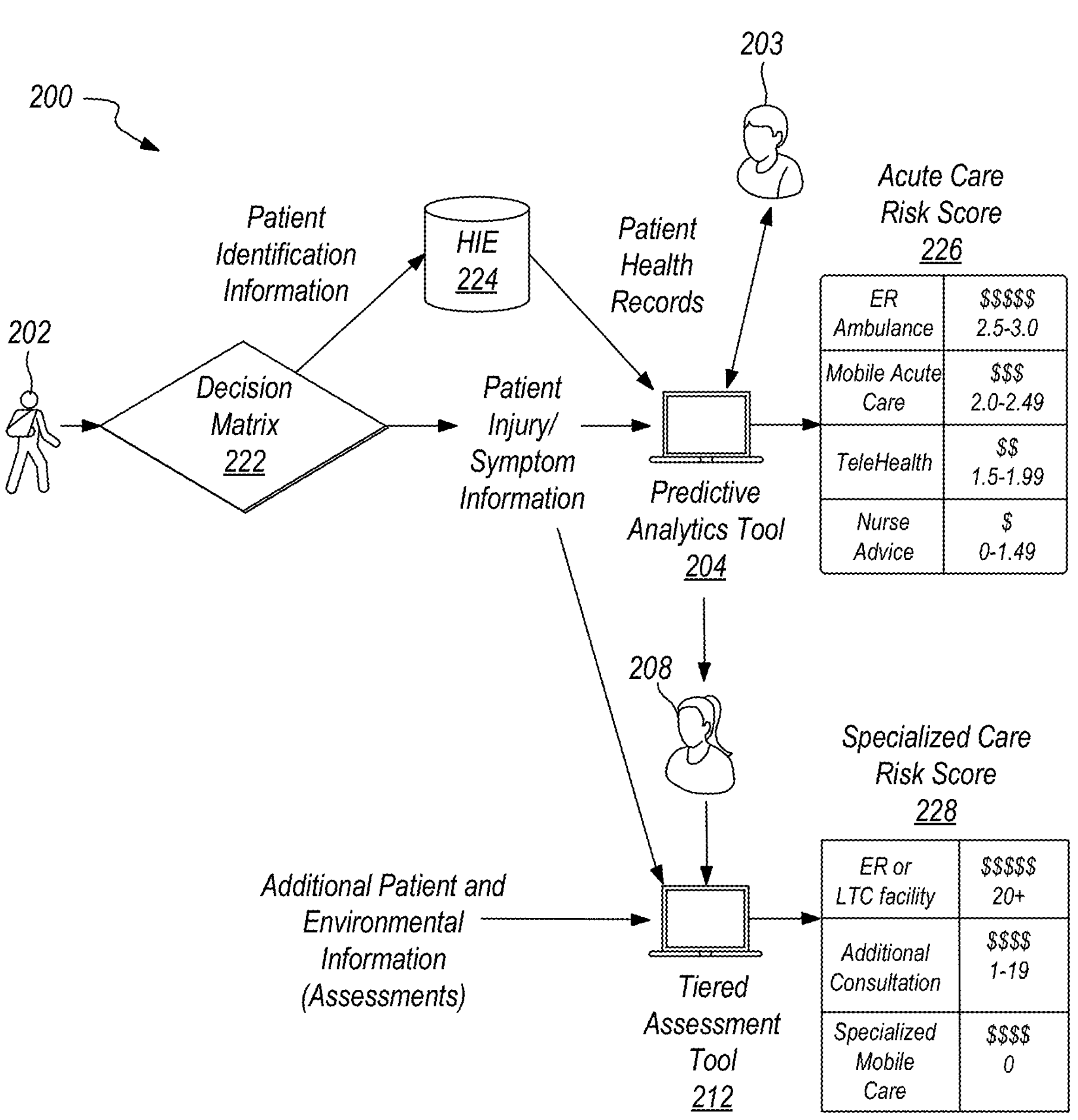
FIG. 2 illustrates a second example flowchart illustrating a patient using a personalized predictive analytics tool and a tiered assessment tool to right-size the patient's access to health care services.

FIG. 2 illustrates a second example flowchart 200 illustrating a patient 202 using a personalized predictive analytics decision engine (or predictive analytics tool) 204 and a tiered assessment tool 212 to right size the patient's access to health care services. The patient 202 accesses a decision matrix 222, which links the patient 202 to the predictive analytics tool 204. In various implementations, the decision matrix 222 is accessed using a telephone-based or an Internet-based interface to input data into the decision matrix 222.

The interface and decision matrix 222 (e.g., an online questionnaire, automated question/answer telephone interface or a live person asking questions of the patient 202 over the telephone or videoconference) collects two types of information from the patient 202. The first type of information is identifying information (e.g., the patient's name, date of birth, sex, social security number, driver's license number, home address, telephone number, etc.). The identifying information identifies the patient 202 to the predictive analytics tool 204 and allows the predictive analytics tool 204 to pull any available and relevant community health records on the patient 202 from a health information exchange (HIE) 224. The HIE 224 outputs community health records on the patient 202 that may provide input variables for the predictive analytics tool 204 including, but not limited to, the patient's past medical history, past surgical history, hospitalization(s), medication history, allergies, laboratory testing results, etc.

The second type of information collected from the patient 202 via the interface and decision matrix 222 is a description of the injury and/or symptoms that the patient 202 is experiencing, which may be collected via an evidence-based technology decision and data collection tree for presenting symptoms to the predictive analytics tool 204. A combination of the input variables from the HIE 224 and the patient's description of the injury and/or symptoms are input into the predictive analytics tool 204 and the predictive analytics tool 204 transforms the input data into an acute care risk score (numerical and/or visual) 226 indicating the overall urgency of the patient's illness or injury and/or a recommendation on acute care services for the patient 202. The predictive analytics tool 204 provides the patient 202 and/or the patient's health care professional(s) (or assigned clinical staff) 203 with a data-driven care recommendation, which, in conjunction with judgment from the patient's health care professional(s) 203 helps to drive the right care, at the right time, for the patient 202.

The predictive analytics tool 204 may use any relevant scale for scoring the urgency and/or severity of the patient's illness or injury (an overall risk factor). One example is a 3-tier scale with "Red" or "2.5-3.0" score indicates that the patient's illness or injury is severe and/or access to acute care services is urgent for the patient's well-being. A "Yellow" or "1.5-2.49" score indicates that the patient's illness or injury is significant and/or access to acute care services is semi-urgent for the patient's well-being. A "Green" or "0-1.49" score indicates that the patient's illness or injury is mild and/or access to acute care services is not urgent.

More specifically, if the patient's risk score 226 is very high (e.g., 2.5-3.0), the predictive analytics tool 204 may recommend to the patient 202 and/or the patient's health care professional(s) 203 that the patient 202 immediately visit an ER or call for ambulatory service. In some implementations, the predictive analytics tool 204 may be used by the patient's health care professional(s) 203 to call 911 on behalf of the patient 202. This is typically the most expensive acute care service ($$$$$) and is often handled by individual municipalities. The predictive analytics tool 204 may also be used to reserve an ER and/or ambulance service for the highest risk scores.

If the patient's risk score 226 is moderately high (e.g., 2.0-2.49), the predictive analytics tool 204 may recommend to the patient 202 and/or the patient's health care professional(s) 203 a mobile acute care unit for the patient 202. This is a mobile unit that has sufficient resources to come to the patient's location (e.g., their home) and treat or diagnose them on-site. In some implementations, the predictive analytics tool 204 may coordinate the mobile care unit on behalf of the patient 202. The mobile acute care unit is a lower cost option ($$$) for acute care services than an ER or ambulatory service and may provide the patient 202 with more rapid and less stressful treatment.

If the patient's risk score 226 is moderately low (e.g., 1.5-1.99), the predictive analytics tool 204 may recommend to the patient 202 and/or the patient's health care professional(s) 203 a telemedicine care service for the patient 202. The telemedicine care service can remotely diagnose the patient's illness or injury, and in some cases diagnose and/or treat the patient's illness or injury. The telemedicine care service may include telephonic interaction, secure text messaging, and/or video interaction with the patient 202, in various example implementations. The predictive analytics tool 204 may connect the patient 202 to the telemedicine care service directly. The telemedicine care service is a relatively low cost ($$) acute care service that may provide the patient 202 with very rapid service.

If the patient's risk score 226 is very low (e.g., 0-1.49), the predictive analytics tool 204 may recommend a nurse hotline to the patient 202 and/or the patient's health care professional(s) 203 for guidance in treating the patient's illness or injury. In some implementations, the predictive analytics tool 204 may connect the patient 202 to the nurse hotline directly. The nurse hotline is a very low-cost acute care service that may provide the patient 202 with very rapid service at a very low or zero cost ($).

In some implementations, the patient 202 receives a visit from a mobile acute care unit as described above, but the mobile acute care unit is not able to provide the care required by the patient 202 within an acceptable risk tolerance. In prior art solutions, this would likely lead to the patient 202 visiting the ER and/or being admitted to an SNF to receive the appropriate level of care. If a health care professional 208 on-site with the mobile acute care unit believes that the patient 202 is capable of being treated safely within their home using higher level, additional, or different clinical resources, the health care professional 208 may trigger the tiered assessment tool 212, which is used to provide an analysis above and beyond that of the predictive analytics tool 204 to further assess the patient, their home, and the capabilities of one or more available specialized mobile care units. Following an input of additional patient and environmental information, taking into account information already input into the predictive analytics tool 204, the tiered assessment tool 212 is used by the health care professional 208 to help determine if a specialized mobile care unit is appropriate to provide in-home care for the patient within an acceptable level of risk.

Similar to the risk score 226 for the predictive analytics tool 204, the tiered assessment tool 212 outputs one or more specialized care risk scores 228 for use in evaluating whether the specialized mobile care unit is appropriate for the patient within an acceptable level of risk. In the example implementation shown, for a specialized care risk score 228 of 0.0, the tiered assessment tool 212 recommends to the health care professional 208 a specialized mobile care unit to render further care to the patient. For a specialized care risk score 228 between 1 and 19, the tiered assessment tool 212 suggests that the health care professional 208 consult with a specialized mobile care unit to determine whether specialized mobile care is appropriate for the patient within the acceptable level of risk. For a specialized care risk score 228 at or above 20, the tiered assessment tool 212 recommends to the health care professional 208 that the patient 202 immediately visit an ER/Hospital or SNF. The specialized mobile care unit is a lower cost option ($$$$) for health care services than hospital in-patient services and admission to an SNF and may provide the patient 202 a less stressful treatment in the comfort of their home.

In some implementations, the specialized mobile care unit is capable of services equivalent to much of which offered at an emergency room and/or hospital (i.e., hospital-level care). In other implementations, the specialized mobile care unit is capable of services equivalent to much of which offered at an SNF (i.e., SNF-level care). In still further implementations, the specialized mobile care unit is capable of services beyond that of the mobile acute care unit, but not equivalent to that available at another specific health care facility.

Should the tiered assessment tool 212 recommend the specialized mobile care unit, the mobile acute care unit may consult or confer with a specialized mobile care team and confirm selection of a specialized mobile care service for the patient 202. The specialized mobile care unit may be dispatched to render the appropriate level of care to the patient 202 within the patient's home (e.g., hospital-level or SNF-level care). Notably, while specialized mobile care ($$$$) may be more expensive than the mobile acute care ($$$), it is less expensive than a visit to the hospital or admission to an SNF ($$$$$). Further, the patient 202 may be happier with the specialized mobile care as it is rendered in the patient's home.

An example implementation of the tiered assessment tool 212 includes a series of assessments, examples of which are described below. A minimal requirements assessment (also referred to as a threshold evaluation) determines if: 1) the patient's insurance will cover specialized mobile care (i.e., patient eligibility); 2) if the patient 202 is at least 18 years old; and 3) if the assessments are being completed within preset business hours for a specialized care team. If the answer to any one or more of the minimal requirement queries is no, the tiered assessment tool 212 stops the analysis and recommends that the patient 202 be escalated to another care option (e.g., the ER/hospital). In various implementations, the minimal requirements assessment (also referred to as a threshold evaluation) may be conducted in-person by a mobile acute care unit or remotely.

A decision-making assessment determines if: 1) the patient 202 or a primary decision maker has full decision-making capacity; and 2) if a shared decision-making conversation between the health care professional 208 associated with the mobile acute care unit and the patient 202/decision maker resulted in a desire to move forward with specialized mobile care. If the answer to any one or both of the decision-making assessment queries is no, the tiered assessment tool 212 stops the analysis and recommends that the patient 202 utilize another care option (e.g., the ER/hospital).

A medical acuity appropriateness assessment may run one or more query sets directed to the patient's medical acuity. As an example, a general medical acuity appropriateness assessment may determine if: 1) the mobile acute care unit is unable to establish peripheral intravenous access to the patient 202 (0/yes or 20/no); 2) the patient 202 has an active secondary condition making in-home hospital-level care impractical (e.g., active (non-prostate) cancer, end-stage renal disease on HD (0-20); 3) a primary diagnosis would require multiple or routine administrations of narcotics for pain control (0-20); 4) the patient 202 cannot independently ambulate to a bedside commode or has no in-home support to enable use of a bedside commode (0-20); 5) the patient 202 is likely to require any of the following procedures: computed tomography, magnetic resonance imaging, endoscopic procedure, blood transfusion, cardiac stress test, or surgery (0-20).

The scores in parentheses for the general medical acuity appropriateness assessment may be individually assessed. For example, a score of 0 indicates that the patient 202 is eligible for specialized mobile care based on their general medical acuity. A score of 1-19 indicates that the patient 202 may be eligible for specialized mobile care based on their general medical acuity, with consultation and approval from the specialized mobile care team. A score 20 or above indicates that the patient 202 is not eligible for specialized mobile care based on their general medical acuity. The patient 202 may then be referred to another care option (e.g., the ER/Hospital). Further, the scores in parentheses for the general medical acuity appropriateness assessment are additive, and a total score may also be judged against thresholds for rendering specialized mobile care. This yields a vast number of possible scores and resulting recommendations based on comparing the scores against a variety of thresholds for rendering specialized mobile care.

A specific medical acuity appropriateness assessment is directed to a specific illness or injury that the patient 202 may have, as determined by the patient's medical history and/or assessment by the mobile acute care unit. For example, if the patient 202 has known diabetes, a blood sugar medical acuity appropriateness assessment may determine if: 1) the patient 202 is on oral medication (0 or 1); 2) the patient 202 on insulin at baseline (0 or 1); and 3) does the mobile acute care team/specialized mobile care team anticipate medications that will worsen blood glucose control (e.g., they anticipate prescribing prednisone) (0 or 1).

Additional specific medical acuity appropriateness assessments (also referred to as diagnosis-related grouping (DRG) assessments) may be conducted as appropriate for the patient 202. In some cases, whether or not the patient 202 qualifies for hospital in-patient care is taken into consideration when determining if the patient 202 is eligible for specialized mobile health care.

The scores in parentheses for each specific medical acuity appropriateness assessment may be individually assessed. For example, a score of 0 indicates that the patient 202 is eligible for specialized mobile care based on their specific medical acuity. A score of 1 indicates that the patient 202 may be eligible for specialized mobile care based on their specific medical acuity, with consultation and approval from the specialized mobile care team. The scores in parentheses for each specific medical acuity appropriateness assessment may also be additive, and a total score is judged against thresholds for rendering specialized mobile care. In some cases, there is an upper limit where the patient is not eligible for specialized mobile care based on their specific medical acuity. The patient 202 may then be referred to another care option (e.g., the ER/hospital).

An environmental assessment is directed to conditions specific to the patient's home (including both patient-focused safety factors and provider-focused safety factors). For example, the environmental assessment may determine if: 1) the patient's home has running water (0/yes or 20/no); 2) the patient's home has electricity (0/yes or 20/no); 3) the patient's home has air conditioning (e.g., during May-August, geographic location dependent) (0/yes or 20/no); 4) the patient's home has heat (e.g., during September-April, geographic location dependent) (0/yes or 20/no); 5) the patient's bedroom location within their home (other than main level: 2); 6) how many vertical steps it takes to enter the patient's home (none: 0, 1-4: 10, 4+: 20); 7) the patient's general home condition as either cluttered or visibly unclean (0-20); 8) the presence of regular smokers within the patient's home (yes: 2); 9) the presence of regular smokers within the patient's home and the patient requires oxygen (yes: 20); 10) detectable previous presence of smokers in the home (yes: 2); 11) current evidence of rodent or insect infestation (e.g., bedbugs) (yes: 20); 12) presence of pet(s) that pose a safety concern for a health care provider and/or pose a concern about the patient's ability to continue to care for the pet(s) (yes: 20); 13) other significant environmental safety concerns for the health care provider and/or the patient (e.g., presence of weapons, geographic location, etc.) (yes: 20); 14) patient's home located within 7 miles of an appropriate emergency medical facility (e.g., a hospital) (no: 20); and 15) presence of data connectively issues for remote monitoring systems (0/yes or 20/no).

The scores in parentheses for the environmental assessment may be individually assessed. For example, a score of 0 indicates that the patient 202 is eligible for specialized mobile care based on their environmental assessment. A score of 1-19 indicates that the patient 202 may be eligible for specialized mobile care based on their environmental assessment, with consultation and approval from the specialized mobile care team. A score 20 or above indicates that the patient 202 is not eligible for specialized mobile care based on their Environmental Assessment. The patient 202 may then be referred to another care option (e.g., the ER). Further, the scores in parentheses for the environmental assessment are additive, and a total score may be judged against thresholds for rendering specialized mobile care.

A social assessment is directed to the patient's social situation. For example, the social assessment may determine: 1) the availability of social support (friends and/or family) to the patient 202 (24/7: 0, 8+ hours and day and all night: 2, 4-8 hours per day: 6, 1-4 hours per day: 10, none: 14); 2) if the patient 202 appears to actively suffer from substance abuse (0/no or 20/yes); 3) if the patient 202 is a current smoker (0/no or 2/yes); 4) if the patient 202 is on hemodialysis or has another medical condition where they receive medical care greater than 3 times a week (0/no or 20/yes); and 5) the patient 202 has reasonable access to food and food preparation materials and space (0/yes or 20/no).

A clinical assessment is directed to the patient's injury or illness. The tiered assessment tool 12 may use hospital-level clinical assessments to evaluate the possibility of rendering hospital-level in the patient's home. Similarly, the tiered assessment tool 12 may use SNF clinical assessments to evaluate the possibility of rendering SNF level care in the patient's home.

The scores in parentheses for the social assessment may be individually assessed. For example, a score of 0 indicates that the patient 202 is eligible for specialized mobile care based on their social assessment. A score of 1-19 indicates that the patient 202 may be eligible for specialized mobile care based on their social assessment, with consultation and approval from the specialized mobile care team. A score 20 or above indicates that the patient 202 is not eligible for specialized mobile care based on their social assessment. The patient 202 may then be referred to another care option (e.g., the ER). Further, the scores in parentheses for the social assessment are additive, and a total score may be judged against thresholds for rendering specialized mobile care.

The scoring provided above are examples only. Actual scoring and weights per question may vary based on the capabilities of the specialized mobile care units, and risk tolerances of the patient 202 and the service running the specialized mobile care units. Further, there may be additional or fewer assessments conducted to evaluate the patient 202 than that described above. In other implementations, the output scores of each assessment are averaged, with weighting factors corresponding to the relative importance of the assessment or underlying factors to determine an overall composite tiered assessment score for the mobile acute care team/specialized care team to use to determine whether specialized in-home care is appropriate for the patient 202.

In various implementations, the weighting factors applied to the environmental/social evaluations may automatically adjust based on the clinical evaluation. For example, if the clinical evaluation indicates that the patient suffers from a condition directed to the patient's respiratory system, conditions or factors in the environmental evaluation that directly impact the patient's respiratory system (e.g., the presence of smokers in the patient's home) are weighted at a higher level than for other clinical evaluations that are not specifically directed to the patient's respiratory system (e.g., a blood disorder).

FIG. 3 illustrates an example patient on-boarding user interface 300 for a predictive analytics tool (also referred to herein as a first stage of a tiered assessment) to right-size the patient's access to acute care services. In various implementations, the user interface 300 is accessed directly by a human representative (or user) for the predictive analytics tool. The human representative interacts with the patient and asks relevant questions to accurately fill out the user interface 300. In other implementations, the user interface 300 is presented directly to the patient and the patient (or user) directly inputs his/her data via the user interface 300.

The user interface 300 includes an on-boarding patient field 302 where the user (a human representative or patient) enters the patient's name, here "Francisco Milner." A request type field 304 permits the user to enter what type of care the patient is requesting, here "911 care." An origin phone number field 306 is either automatically populated or manually entered by the user, here "111-222-3333." A source field 308 permits the user to identify the relation between the user of the tool (or person directing use of the tool) and the patient (here, the user is the patient). A power of attorney field 310 permits the user to indicate whether the patient makes his/her own medical decisions, or if another individual has been granted medical power of attorney over the patient.

A chief complaint field 312 permits the user to enter words or abbreviations that indicate the patient's chief complaint, herein "n/v", which is shorthand for "nausea/vomiting." The tool may store and automatically present screening protocol options 314 for the chief complaint in real-time as the user enters words or abbreviations into the chief complaint field 312 for risk stratification. In various implementations, the user may have the option to enter multiple complaints. The user also has the option to use a case notes field 316 to enter custom notes regarding the patient for later retrieval within the tool.

Additional information may be input into the tool via additional tabs accessible from the user interface 300. For example, in a market tab 318, the user enters the relevant geographic market that serves the patient's physical location where care is requested, here 80027—Denver. In a scheduling tab 320, the user is able to view the acute care services available to the user and schedule those resources appropriately according to the patient's risk score (calculated later). In a demographics tab 322, the user is able to enter demographic information (e.g., age, sex, height, weight, etc.) regarding the patient. In a channel tab 326, the user is able to enter or view the course of the patient's request for acute care services (e.g., 911, the patient's direct access, or a health care partner, such as a senior community, a home health service, a provider group, a health system, care management staff, skilled nursing facility (SNF) staff, etc.). In a location tab 328, the user enters one or more of the patient's current physical location, the patient's mailing address, and the patient's billing address. In an Athena patient tab 330, the user enters the patient's Athena ID (if applicable). In an insurance tab 332, the user enters the patient's health insurance information. In a billing tab 334, the user enters the patient's billing information (e.g., billing address, credit card information, etc.). In a care plan tab 336, the user can enter the patient's care plan (if applicable). In a providers tab 338, the user can enter a listing of the patient's care providers. Progress bar 340 indicates the percent completion of the patient on-boarding user interface 300, here 50%.

Once the on-boarding process is complete and the patient's acute care risk score is calculated (see e.g., acute care risk score 226 of FIG. 2), a health care professional reviews the patient's on-boarding information and acute care risk score and determines if the patient is eligible for mobile acute care rendered in the patient's home. If so, the patient is queued to receive mobile acute care unit at their home to render treatment to the patient.

FIG. 4 illustrates an example dashboard 400 of assigned acute care patients for a specific market (here, DEN (23)). The dashboard 400 organizes patients in sequencing categories 402, specifically "Upcoming," "In Queue," "Assigned," "Billing," "Follow Up," and "Archive." "Upcoming" patients have been approved to receive mobile acute care rendered in the patient's home but have not been scheduled to receive treatment. "In Queue" patients have been scheduled to receive treatment but have not yet been assigned a specific mobile acute care unit to render treatment. "Assigned" patients have been scheduled and assigned a specific mobile acute care unit to render treatment. "Assigned" patients are typically soon to receive treatment (within 8 hours or within 24 hours) or are currently receiving treatment by their assigned mobile acute care unit. "Billing" patients have been treated by their assigned mobile acute care unit and are now going through a billing process for services rendered. "Follow-up" patients have been treated and billed but have been identified by their assigned mobile acute care unit as needing future follow-up by a health care professional. "Archive" patients have completed their treatment and are archived.

The illustrated dashboard 400 is of the "Assigned" patient category and illustrates two mobile acute care units (DEN CAR 01 and DEN CAR 02) and their respective assigned patient loads 404, 406. Mobile acute care unit information displays 412, 414 shows each of the two mobile acute care units have operating hours (here, DEN CAR 01 is operating between 7 am and 4 pm, while DEN CAR 02 is operating between 10 am and 7 pm) and have images of their assigned personnel, respectively. Specifically, each of DEN CAR 01 and DEN CAR 02 includes three individuals per mobile acute care unit. At least one of the assigned personnel for each of the mobile acute care units is a qualified health care professional capable of performing acute care services on their assigned patients.

DEN CAR 01 is assigned three patients, one of which DEN CAR 01 is identified as "On Scene" with the patient by status identifiers 408, and two of which DEN CAR 02 is identified as "En Route" to. Timing window 410 provides an estimated time of completion (ETC) with the "On Scene" patient (here, estimated at 11:38 am DEN (MST), with an estimated variability between 11:00 am and 12:30 pm. The Timing window 410 provides an estimated time of arrival (ETA) for each of the "En Route" patients.

DEN CAR 02 is assigned Francisco Milner as is identified as "On Scene" with the patient by status identifier 408. A timing window 410 provides an estimated time of completion (ETC) with the patient (here, estimated at 1:58 pm DEN (MST), with an estimated variability between 1:45 pm and 2:45 pm. Further, a subset of data previously collecting using the predictive analytics tool for Francisco Milner is displayed on the dashboard 400, such as the patient's home address (here, 123 Linden blvd #3; Denver, CO 80211), the patient's telephone number (here, 303-123-4567), the service to be rendered (here, acute care), and the patient's primary affliction (here, an Upper Respiratory Infection).

Mr. Milner is illustrated as an "Advanced Care Candidate" by advanced care indicator 416, which indicates to DEN CAR 02 that the patient meets basic threshold requirements or satisfies a threshold evaluation (e.g., insurance coverage for in-home care (patient eligibility), age (e.g., 18-65), location (within 7 miles of an emergency facility, and reported condition) for specialized mobile health care, if needed. Selecting Mr. Milner takes the individual navigating the dashboard 400 to a display providing additional detail regarding Mr. Milner, including a selector to "EVALUATE FOR ADVANCED CARE" if the individual navigating the dashboard 400 believes that service to be potentially appropriate for the patient.

In some instances, selecting the "EVALUATE FOR ADVANCED CARE" selector triggers a confirmation screen. The confirmation screen requests that the individual navigating the dashboard 400 confirm that they wish to begin the evaluation for specialized mobile care (also referred to herein as a second stage of a tiered assessment). Selecting "CONFIRM" takes the individual to dashboard 500 of FIG. 5.

FIG. 5 illustrates an example dashboard 500 for an ADVANCED CARE DIAGNOSIS portion of an ADVANCED CARE EVALUATION of a patient (here, Mr. Milner). The ADVANCED CARE DIAGNOSIS displays a number of conditions that Mr. Milner may be suffering from that are eligible for treatment using specialized mobile care in Diagnosis Related Grouping (DRG) display 502. As shown in dashboard 500 of FIG. 5, the individual navigating the dashboard 500 may select one or more of the displayed options (here, Pneumonia) that apply to Mr. Milner.

The dashboard 500 further has an ADVANCED CARE EVALUATION status display 504 that provides an overall picture of the ADVANCED CARE EVALUATION status of steps completed vs. not yet completed. Here, the ADVANCED CARE EVALUATION status display 504 indicates that Mr. Milner has appropriate insurance for specialized mobile care (here, UnitedHealthCare Medicare Advantage) and that the individual has selected an appropriate condition that is eligible for treatment using specialized mobile care (here, Pneumonia). The ADVANCED CARE EVALUATION status display 504 further indicates that a HOME ASSESSMENT has not yet been completed (see dashboard 600 of FIG. 6, discussed below).

The ADVANCED CARE EVALUATION status display 504 further includes a risk indicator (or indicator of risk) 508 that places the risk score given the information collected so far on a recommendation scale (here, "LOW RISK" to "MEDIUM RISK" to "HIGH RISK"). In other implementations, a similar result may be depicted visually using green, yellow, and red lights, in addition to or in lieu of the depicted textual recommendation scale. Here, the risk indicator 508 indicates that given the information collected so far, Mr. Milner is at a relatively low risk for using specialized mobile care. The individual may use the "SAVE CLINICAL ASSESSMENT" selector 506 to proceed to the next portion of the ADVANCED CARE EVALUATION, illustrated as dashboard 600 of FIG. 6.

FIG. 6 illustrates an example dashboard 600 for a HOME ASSESSMENT portion of an ADVANCED CARE EVALUATION of a patient (here, Mr. Milner). The HOME ASSESSMENT displays a number of conditions of Mr. Milner's home as it relates to the safety of both Mr. Milner and the specialized hospital mobile care unit should specialized hospital mobile care be authorized for Mr. Milner in Home Assessment display 602. As shown in dashboard 600 of FIG. 6, the individual navigating the dashboard 600 may select one or more of the displayed options (here, all YES answers) that apply to Mr. Milner's home.

The dashboard 600 further has an ADVANCED CARE EVALUATION status display 604 that provides an overall picture of the ADVANCED CARE EVALUATION status of steps completed vs. not yet completed. In addition to the insurance and advanced care diagnosis steps described above and illustrated as complete in dashboard 500, the Home Assessment is now indicated as "Passed" responsive to the individual indicating YES answers to all the Home Assessment that apply to Mr. Milner's home. The ADVANCED CARE EVALUATION status display 604 further indicates that given the information collected so far, Mr. Milner is at a relatively low risk for using specialized mobile care. Should Mr. Milner remain eligible for specialized hospital mobile care following completion of the HOME ASSESSMENT, the individual may further use the "SAVE HOME ASSESSMENT" selector 606 and view a confirmation screen (see confirmation screen 800 of FIG. 8, discussed below).

Alternatively, as shown in dashboard 700 of FIG. 7, if the individual selects any of the displayed options (here, NO to whether Mr. Milner's home has running water) in Home Assessment display 702 that render Mr. Milner ineligible for specialized hospital mobile care, the ADVANCED CARE EVALUATION status display 704 indicates that the Home Assessment has "Failed" and that Mr. Milner is at a relatively high risk for using specialized mobile care. Further, the dashboard 700 displays to the individual navigating the dashboard 700 that they may escalate Mr. Milner to an emergency department using escalation selector 706 without completing the ADVANCED CARE EVALUATION.

FIG. 8 illustrates confirmation screen 800 for completion of a HOME ASSESSMENT portion of an ADVANCED CARE EVALUATION of a patient (here, Mr. Milner). The confirmation screen 800 includes a Home Assessment display 802 that indicates that Mr. Milner is cleared for specialized mobile care and instructs the mobile acute care unit to contact the advanced mobile care team to complete the ADVANCED CARE EVALUATION. The individual may then use a "CONTINUE TO WORK-UP" selector 806 to proceed to the next portion of the ADVANCED CARE EVALUATION, which is illustrated as dashboard 900 of FIG. 9.

FIG. 9 illustrates an example dashboard 900 for a first page of a CLINICAL ASSESSMENT portion of an ADVANCED CARE EVALUATION of a patient (here, Mr. Milner). The first portion of the CLINICAL ASSESSMENT includes a variety of tasks for the mobile acute care unit to complete (e.g., LABS, IMAGING, etc.) in the Clinical Assessment display 902, which may be specific to the patient's indicated illness(es) or injury(ies), in order to admit the patient for specialized mobile health care. Following completion of the assigned tasks, the individual navigating the dashboard 900 may then use a "TRANSITION TO ADVANCED CARE" selector 906 to move to a second page of the CLINICAL ASSESSMENT portion, as shown in dashboard 1000 of FIG. 10.

FIG. 10 illustrates an example dashboard 1000 for a second page of the CLINICAL ASSESSMENT portion of an ADVANCED CARE EVALUATION of a patient (here, Mr. Milner). The second page of the CLINICAL ASSESSMENT includes a MEDICAL CRITERIA display 1002 for the mobile acute care unit to enter and select medical criteria specific to the patient, as appropriate, and an invitation to call the specialized mobile health care team to consult or confer on whether it is agreed to admit the patient for specialized mobile health care. The consultation between the mobile acute care unit and the specialized mobile care (or Advanced Care) team is used to jointly determine whether to render additional services using the specialized mobile care unit within an accepted risk level. Following a successful consultation where the specialized mobile health care team agrees to admit the patient for specialized mobile health care treatment, the individual navigating the dashboard 1000 may use a "GET CONSENT" selector 1006 to get the patient's formal consent for specialized mobile health care to complete the patient's intake for specialized mobile health care.

A default type and duration of specialized mobile health care is initially set for the patient during intake. However, changes in type and frequency of patient visits may occur iteratively during the course of the treatment based on how patient responds to the specialized mobile health care treatment. Further, the specialized mobile health care treatment may transition to a different level of care (e.g., maintenance mobile health care treatment) once the patient is sufficiently treated and no longer qualifies for in-home specialized (e.g., hospital-level) care.

In various implementations, there are condition-specific assessments for specialized mobile health care treatment that are performed in addition to the described environmental assessment(s) and clinical assessment(s). The condition-specific assessments are directed at evaluating the patient's condition and symptoms and determining how appropriate specialized mobile health care treatment is in view of the patient's specific condition and symptoms. Several example condition-specific assessments are described below, including assessments for each of cellulitis, congestive heart failure (CHF), chronic inflammatory lung disease (COPD), pneumonia, and urinary tract infections. These are provided as examples only, as in practice there may be many more or different condition-specific assessments incorporated into a tiered assessment tool for determining how appropriate specialized mobile health care treatment is for the patient.

CELLULITIS SPECIFIC APPROPRIATENESS SCREEN (minimal requirement criteria determined from general assessment upstream (see e.g., predictive analytics tool).

1. Clinical diagnosis of cellulitis is highly suspected: If yes, move forward. If no, stop. The patient may still be appropriate for specialized mobile health care treatment if the patient meets diagnostic criteria for another specific condition.

2. Suspect sepsis refractory to IV fluid resuscitation and/or needs vasopressor support: If no, move forward. If yes, stop. Patient is deemed not appropriate for specialized mobile health care treatment.

3. Purulent skin infection: If no, move forward. If yes, stop. Patient is deemed not appropriate for specialized mobile health care treatment.

4. Suspicion of infected foreign body/medical device: If no, move forward. If yes, stop. Patient is deemed not appropriate for specialized mobile health care treatment.

5. One or more of these complicating factors: Infected diabetic ulcer or vascular ulcer, necrotizing infection, infection of perineal/vulvar/rectal/orbital area, pregnancy, and surgical site infection: If no, move forward. If yes, stop. Patient is deemed not appropriate for specialized mobile health care treatment.

6. Clinical concern for necrotizing fasciitis including profound tenderness, sclerosis, skin necrosis, hemorrhagic bullae, subcutaneous crepitus, and/or pain out of proportion to exam/erythema: If no, move forward. If yes, stop. Patient is deemed not appropriate for specialized mobile health care treatment.

7. Patient's goals of care are in line with a trial of home treatment (e.g., the patient refuses escalation or strongly prefers home treatment and can verbalize the risk-benefit trade-offs): If yes, move forward. If no, stop. Patient is deemed not appropriate for specialized mobile health care treatment.

8. If the patient passes the foregoing steps, perform the following cellulitis checklist: secure intravenous (IV) access, draw basic metabolic panel including calcium (Chem-8), and consult with specialized mobile health care team. Specialized mobile health care team consultation may include methicillin resistant staphylococcus Aureus (MRSA) risk factors, such as: a history of MRSA infection (1), recent (e.g., within the prior one to two months) hospitalization or surgery (1), residence in a SNF (1), hemodialysis (1). Further risk factors for considering during the consultation include: human immunodeficiency virus (HIV) infection or other immunocompromised state (1), poorly controlled diabetes mellitus (1), bite wound(s) (1), and/or multiple comorbid complications that may be difficult to adequately manage using specialized mobile health care treatment (1). Point values (e.g., "1") are assigned to each risk factor that is present for further scoring the patient's risk in using specialized mobile health care treatment using the tiered assessment tool.

CHF SPECIFIC APPROPRIATENESS ASSESSMENT (minimal requirement criteria determined from general assessment upstream (see e.g., predictive analytics tool).

1. Clinical diagnosis of acute CHF exacerbation is highly suspected: If yes, move forward. If no, stop. The patient may still be appropriate for specialized mobile health care treatment if the patient meets diagnostic criteria for another specific condition.

2. New diagnosis of CHF or the patient requires ICU or step-down level care or continuous telemetry (including has respiratory failure requiring more than nasal cannula or sepsis requiring vasopressor support): If no, move forward. If yes, stop. Patient is deemed not appropriate for specialized mobile health care treatment.

3. Any of: cool extremities/evidence of shock (spontaneous bacterial peritonitis (SBP)<90 and elevated lactate), K+<2.5 or >5.5 with ECG changes, high suspicion for acute coronary syndrome, patient likely to require IV medications for blood pressure (BP) or heart rate (HR) control, arterial oxygen saturation (i.e., SpO2 less than or equal to 90%) despite supplemental oxygen, patient's respirator rate is greater or equal to 30 bpm, patient's heart rate sustained at <40 or >130 bpm: If no, move forward. If yes, stop. Patient is deemed not appropriate for specialized mobile health care treatment.

4. Patient's goals of care are in line with a trial of home treatment (e.g., the patient refuses escalation or strongly prefers home treatment and can verbalize the risk-benefit trade-offs): If yes, move forward. If no, stop. Patient is deemed not appropriate for specialized mobile health care treatment.

5. If the patient passes the foregoing steps, perform the following CHF checklist: secure intravenous (IV) access, draw basic metabolic panel including calcium (Chem-8), perform electrocardiogram (EKG), and consult with specialized mobile health care team. Specialized mobile health care team consultation may include running ADHERE (Acute Decompensated Heart Failure National Registry Algorithm). See e.g., https://www.mdcalc.com/acute-decompensated-heart-failure-national-registry-adhere-algorithm, BUN>42, SBP<115, Creatinine>2.74. Point values (e.g., low risk (0), intermediate risk (1), or high risk (2)) are assigned to each ADHERE risk factor that is present for further scoring the patient's risk in using specialized mobile health care treatment using the tiered assessment tool. High risk cases are not likely appropriate for specialized mobile health care treatment.

Health care professional running the assessment may then consult with a specialized mobile health care team. The specialized mobile health care team consultation may include running GWTG-HF (Get With The Guidelines Heart Failure Risk Score), see e.g., https://www.mdcalc.com/gwtg-heart-failure-risk-score, which evaluates and scores SBP, BUN, Na, Age, HR, Race, COPD. Point values (e.g., low risk (0-33), intermediate risk (34-50), or high risk (51-100)) are assigned to each GWTG-HF risk factor that is present for further scoring the patient's risk in using specialized mobile health care treatment using the tiered assessment tool. High risk cases are not likely appropriate for specialized mobile health care treatment.

Further risk factors for considering during the consultation include: known ejection fraction <35 (1), syncopal episode in the past week (if yes, patient is deemed not appropriate for specialized mobile health care treatment (1)), New arrhythmia on ECG (review with specialized mobile health care team, if true and high risk, not appropriate for specialized mobile health care treatment (1)), and multiple comorbid complications that may not be adequately managed through specialized mobile health care treatment (1). Point values (e.g., "1") are assigned to each risk factor that is present for further scoring the patient's risk in using specialized mobile health care treatment using the tiered assessment tool.

COPD SPECIFIC APPROPRIATENESS ASSESSMENT (minimal requirement criteria determined from general assessment upstream (see e.g., predictive analytics tool).

1. Clinical diagnosis of COPD is highly suspected (patient wheezing, SOB, increased sputum, Hx of COPD in the past): If yes, move forward. If no, stop. The patient may still be appropriate for specialized mobile health care treatment if the patient meets diagnostic criteria for another specific condition.

2. Patient requires ICU or step-down level care or continuous telemetry (including respiratory failure requiring more than nasal cannula or sepsis requiring vasopressor support): If no, move forward. If yes, stop. Patient is deemed not appropriate for specialized mobile health care treatment.

3. BAP-65 and Other Risks (BOR) Score (Score for Acute Exacerbation of COPD), see e.g., https://www.mdcalc.com/bap-65-score-acute-exacerbation-copd. Assign tiered assessment scores as follows: BAP Class I (0), BAP Class II (0), BAP Class III (5), BAP Class IV (20), BAP Class V (20).

4. Patient has an altered Mental Status (evaluated with the context of BUN>24, HR>108, and age 41-64 or >64): If no, move forward. If yes, stop. Patient is deemed not appropriate for specialized mobile health care treatment.

5. Patient has one or more of the following that would likely necessitate non-invasive ventilation or intubation: cyanosis or SpO2<88% despite supplemental O2 (20), marked use of accessory muscles (20), paradoxical chest wall and abdominal movements (20), lethargy and confusion (20), history of hypercapnia requiring previous admissions and/or augmented ventilation (5), known severe COPD at baseline (e.g., forced expiratory volume (FEV1)<51 percent of predicted) (20), signs and symptoms of sepsis or worsening of clinical condition during evaluation (20), multiple comorbid complications that cannot be adequately managed through specialized mobile health care treatment (20), venous blood gas (VBG) shows pH<7.35 (20), patient is an active smoker, needs oxygen, and is unwilling to stop smoking during acute illness (20), patient, support people, or nursing services unable to administer Q1-4 hour nebulizer therapies as needed (20). Point values (e.g., low risk (0), intermediate risk (1-19), or high risk (20+)) are assigned to each risk factor that is present for further scoring the patient's risk in using specialized mobile health care treatment using the tiered assessment tool. High risk cases are not likely appropriate for specialized mobile health care treatment.

6. The patient qualifies for inpatient status. Specifically, despite home and acute treatments, patient is still not breathing comfortably at rest, respiratory rate>30, HR>100, and/or excessive dyspnea that are limiting activities of daily living (ADLs). Patient has severe underlying COPD, frailty, or other complicating factors that make treating this in ambulatory setting impractical (including insufficient support at home). If no to both, move forward. If yes to either or both, stop. Patient is deemed not appropriate for specialized mobile health care treatment. Health care professional running the assessment may then consult with a specialized mobile health care team.

PNEUMONIA SPECIFIC APPROPRIATENESS ASSESSMENT (minimal requirement criteria determined from general assessment upstream (see e.g., predictive analytics tool).

1. Clinical diagnosis of pneumonia highly suspected: If yes, move forward. If no, stop. The patient may still be appropriate for specialized mobile health care treatment if the patient meets diagnostic criteria for another specific condition.

2. Patient requires ICU or step-down level care or continuous telemetry (including has respiratory failure requiring more than nasal cannula or sepsis requiring vasopressor support): If yes, stop. Patient is deemed not appropriate for specialized mobile health care treatment.

3. CURB-65+Oxygenation Score (O-CURB65), see e.g., https://www.mdcalc.com/curb-65-score-pneumonia-severity. Assign tiered assessment scores as follows to CURB-65 score: 0-2 (0), 3 (5), 4-5 (20), confusion (1), BUN>19 (1), respiratory rate (RR)>30 (1), systolic blood pressure (SBP) <90 or diastolic blood pressure (DBP)<60 (1), Age >65 (1), Oxygenation status: >92% on presentation (0), 88-91 on presentation (5), 87 or less on presentation or 88-91 on presentation and doesn't improve with supplemental O2 (20). Point values (e.g., low risk (0), intermediate risk (1-19), or high risk (20+)) are assigned to each risk factor that is present for further scoring the patient's risk in using specialized mobile health care treatment using the tiered assessment tool. High risk cases are not likely appropriate for specialized mobile health care treatment.

4. The patient has multiple comorbid complications that cannot be adequately managed through specialized mobile health care treatment or has 2 or more of the following: broad spectrum antibiotic use in past 3 months (1), recent ICU admission/mechanical ventilation (1), past infection or colonization with MRSA, pseudomonas, or other resistant organism (1), structural lung disease (1), current immunocompromised state (1). If the sum is 0, move forward. If the sum is 1, move forward, but higher (intermediate) risk. If the sum is 2+, stop. Patient is deemed not appropriate for specialized mobile health care treatment.

5. The patient qualifies for inpatient status. Specifically, the patient's peripheral O2 sat<92 percent on RA (or a significant change from baseline), CURB-65 score is greater than or equal to 1 (or CURB-65 score is greater than or equal to 2, if patient's age >65), complicating factors making routine ambulatory pulmonary nodular amyloidosis (PNA) treatment unsafe or not feasible (i.e., inability of the patient to take oral medications, cognitive or functional impairment, etc.). If no to all, move forward. If yes to any one or more, stop. Patient is deemed not appropriate for specialized mobile health care treatment. Health care professional running the assessment may then consult with a specialized mobile health care team.

URINARY TRACT INFECTION (UTI) SPECIFIC APPROPRIATENESS ASSESSMENT (minimal requirement criteria determined from general assessment upstream (see e.g., predictive analytics tool).

1. Clinical diagnosis of complicated UTI is highly suspected: If yes, move forward. If no, stop. The patient may still be appropriate for specialized mobile health care treatment if the patient meets diagnostic criteria for another specific condition.

2. Suspect severe sepsis refractory to IV fluid resuscitation and/or needing vasopressor support: If no, move forward. If yes, stop. Patient is deemed not appropriate for specialized mobile health care treatment.

3. Patient has history of organ transplant: If no, move forward. If yes, stop. Patient is deemed not appropriate for specialized mobile health care treatment.

4. Patient is pregnant: If no, move forward. If yes, stop. Patient is deemed not appropriate for specialized mobile health care treatment.

5. Strong clinical suspicion for nephrolithiasis: If no, move forward. If yes, stop. Patient is deemed not appropriate for specialized mobile health care treatment.

6. Patient's goals of care are in line with a trial of home treatment (e.g., the patient refuses escalation or strongly prefers home treatment and can verbalize the risk-benefit trade-offs): If yes, move forward. If no, stop. Patient is deemed not appropriate for specialized mobile health care treatment.

7. If the patient passes the foregoing steps, perform the following UTI checklist: secure intravenous (IV) access, draw basic metabolic panel including calcium (Chem-8), check urine analysis (UA) and leave the urine culture tube with the patient, and consult with specialized mobile health care team. Specialized mobile health care team consultation may include a discussion of complicating factors, such as: the patient is immunocompromised (1), the patient has a history of urologic anatomical abnormalities (diversion, stents, etc.) (1), the patient has a chronic indwelling catheter (1), the patient has signs or symptoms or urinary tract obstruction (1), the patient has a history of multi-drug resistant organism (1), the patient has multiple comorbid complications that may be difficult to adequately manage using specialized mobile health care (1). If the sum is 0, move forward. If the sum is 1, move forward, but higher (intermediate) risk.

8. The patient qualifies for inpatient status. Specifically, the patient has hemodynamic instability, as indicated by one or more of the following: patient has vital sign abnormality not readily corrected by appropriate treatment within 12 to 24 hours, as indicated by one or more of the following: tachycardia that persists despite appropriate treatment (HR>100) (e.g., volume repletion, treatment of pain, and treatment of underlying cause). If yes to any one or more, stop. Patient is deemed not appropriate for specialized mobile health care treatment.

While the foregoing assessments have condition-specific features, these features may be combined in different ways to create different assessments, or to modify the foregoing assessments.

Figure 11:
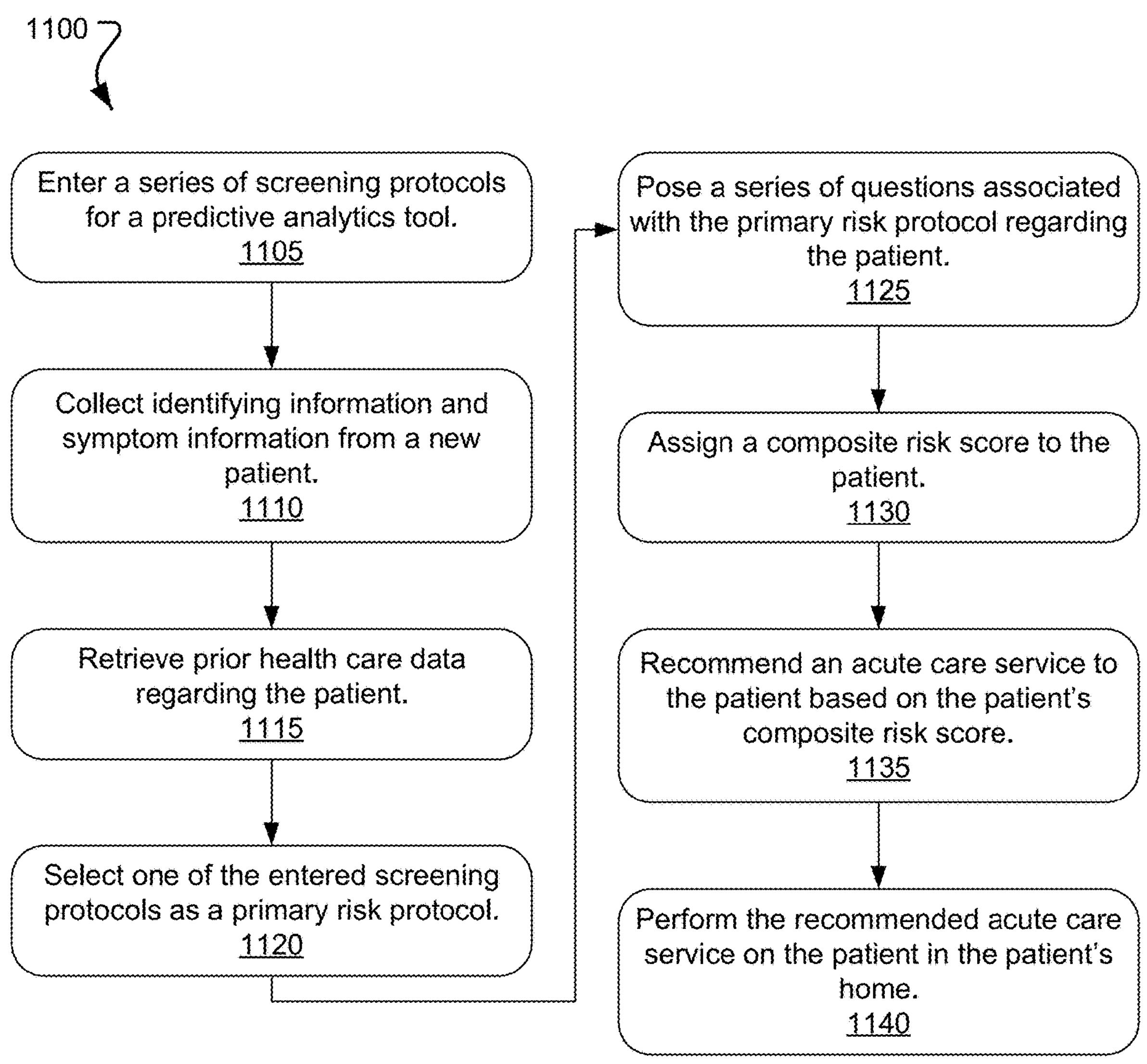
FIG. 11 illustrates example operations for providing right-sized medical care to a patient.

FIG. 11 illustrates example operations 1100 for providing right-sized medical care to a patient. In an entering operation 1105, a user enters a series of screening protocols, each defined by a base score and a series of questions to be posed regarding the patient. The screening protocols each define a potential primary risk protocol to be used to generate a risk score associated with the patient upon entry for a predictive analytics tool. In a collecting operation 1110, a user (the same or a different user from operation 1105) collects data from a new patient, the data including identifying information and symptom information. The identifying information is associated specifically with the patient's identity, demographics, location, etc., while the symptom information is associated specifically with the patient's condition that has triggered the patient to request care using the predictive analytics tool.

A retrieving operation 1115 retrieves prior health care data regarding the patient from a health information exchange using the patient's identifying information. The retrieving operation 1115 may pull information from any available health care database. A selecting operation 1120 selects one of the entered screening protocols as a primary risk protocol based on the patient's symptom information. In various implementations, keywords entered during the collecting operation 1110 regarding the patient's symptoms is compared against keywords associated with each available screening protocol. A user selects the most appropriate available screening protocol as the primary risk protocol.

A posing operation 1125 poses a series of questions associated with the primary risk protocol regarding the patient. In various implementations, an individual risk score is calculated for each answer of each of the questions. Further, time filters may be applied to each of the questions. An assigning operation 1130 assigns a composite risk score to the patient based on the selected primary risk protocol, answers to the series of questions, the identifying information, the symptom information, and the prior health care data. In some implementations, the composite risk score is a combination of the individual risk scores calculated from each of the answers collected during the posing operation 1125, combined with a base score associated with the patient.

A recommending operation 1135 recommends an acute care service to the patient based on the assigned risk score falling within a predetermined range associated with the recommended acute care service. In various implementations, the available options for a recommended acute care service include an ER visit, a visit from a mobile care unit, a telemedicine service, and a nurse advice line. As an example, the highest risk score range is assigned to the ER visit, a medium-high risk score range is assigned to the mobile care unit, a medium-low risk score range is assigned to the telemedicine service, and a low-risk score range is assigned to the nurse advice line. In a performing operation 1140, a medical care provider performs the recommended acute care service on the patient in the patient's home.

FIG. 12 illustrates further example operations 1200 for providing right-sized medical care to a patient. In a performing operation 1205, a medical care provider (or health care professional) member of a mobile acute care unit performs an acute care service on the patient in the patient's home. In some implementations, the performing operation 1205 is the result of the operations 1100 of FIG. 11 for providing right-sized medical care to a patient using a predictive analytics tool, as discussed above. This serves as the entry point for the patient to be evaluated using the tiered assessment tool, as discussed in further detail below. In other implementations, the acute care service is omitted, and the patient is identified for evaluation using the tiered assessment tool by an alternative entry point. For example, the patient may be referred to the tiered assessment tool by a health care professional at a hospital or emergency room in lieu of admission to the hospital. For further example, the patient may be referred to the tiered assessment tool by the patient's primary care physician or a specialist.

In a performing operation 1210, the tiered assessment tool performs a threshold evaluation to determine patient eligibility for a specialized health care service to be rendered in the patient's home. The threshold evaluation includes threshold factors for the patient to be considered for specialized health care service, such as insurance coverage for in-home care, age, and distance from an emergency room should escalation be required. The threshold evaluation may be conducted on-site at the patient's home and/or remotely. A collecting operation 1215 collects the threshold evaluation results within the tiered assessment tool.

In a performing operation 1220, a health care professional associated with the mobile acute care unit performs an environmental assessment of the patient's home. The environmental assessment includes both patient-focused safety factors and provider-focused safety factors. Further, the environmental assessment may include social support factors for the patient. In implementations where the patient's entry point into the tiered assessment tool was not mobile acute care, a dedicated tiered assessment team may be dispatched to the patient's home to conduct the environmental assessment and the following clinical assessment. A collecting operation 1225 collects the environmental assessment results with the tiered assessment tool.

In a performing operation 1230, the health care professional associated with the mobile acute care unit performs a clinical assessment of the patient. In various implementations, the clinical assessment is for providing one of hospital-level and long-term nursing care in the patient's home. A collecting operation 1235 collects the clinical assessment results with the tiered assessment tool.

In an assigning operation 1240, the tiered assessment tool assigns a specialized care risk score based on the environmental assessment and the clinical assessment. The specialized care risk score is attributable to risk in providing the specialized health care service in the patient's home. In a presenting operation 1245, the tiered assessment tool presents an indicator of risk in rendering the specialized health care service in the patient's home. In various implementations, the indicator of risk is in the form of a position of the specialized care risk score on a recommendation scale.

In an evaluating operation 1250, the health care professional evaluates the specialized care risk score at least in part on its position on the recommendation scale. The health care professional may also confer with another health care professional associated with the specialized health care service in the evaluating operation 1250. In an approving operation 1255, the health care professional approves the specialized health care service for the patient in the patient's home should the health care professional find the specialized care risk score acceptable and have confidence in a positive outcome for the patient. This confidence is based at least on their professional judgement, and further based in part on their conference with the health care professional associated with the specialized health care service.

An equipping operation 1260 equips the patient's home with one or more pieces of specialized equipment (e.g., a medical grade bed, imaging equipment, personal emergency response system (PERS), a medical data link over the Internet, etc.) based on the environmental assessment and the clinical assessment in advance of rendering the specialized health care service in the patient's home. In various implementations, the tiered assessment tool outputs a list of specialized equipment for satisfying the equipping operation 1260. In a rendering operation 1265, a specialized mobile care unit renders the specialized health care service in the patient's home.

The embodiments of the invention described herein are implemented as logical steps in one or more computer systems. The logical operations of the present invention are implemented (1) as a sequence of processor-implemented steps executing in one or more computer systems and (2) as interconnected machine or circuit modules within one or more computer systems. The implementation is a matter of choice, dependent on the performance requirements of the computer system implementing the invention. Accordingly, the logical operations making up the embodiments of the invention described herein are referred to variously as operations, steps, objects, or modules. Furthermore, it should be understood that logical operations may be performed in any order, unless explicitly claimed otherwise or a specific order is inherently necessitated by the claim language.

Figure 13:
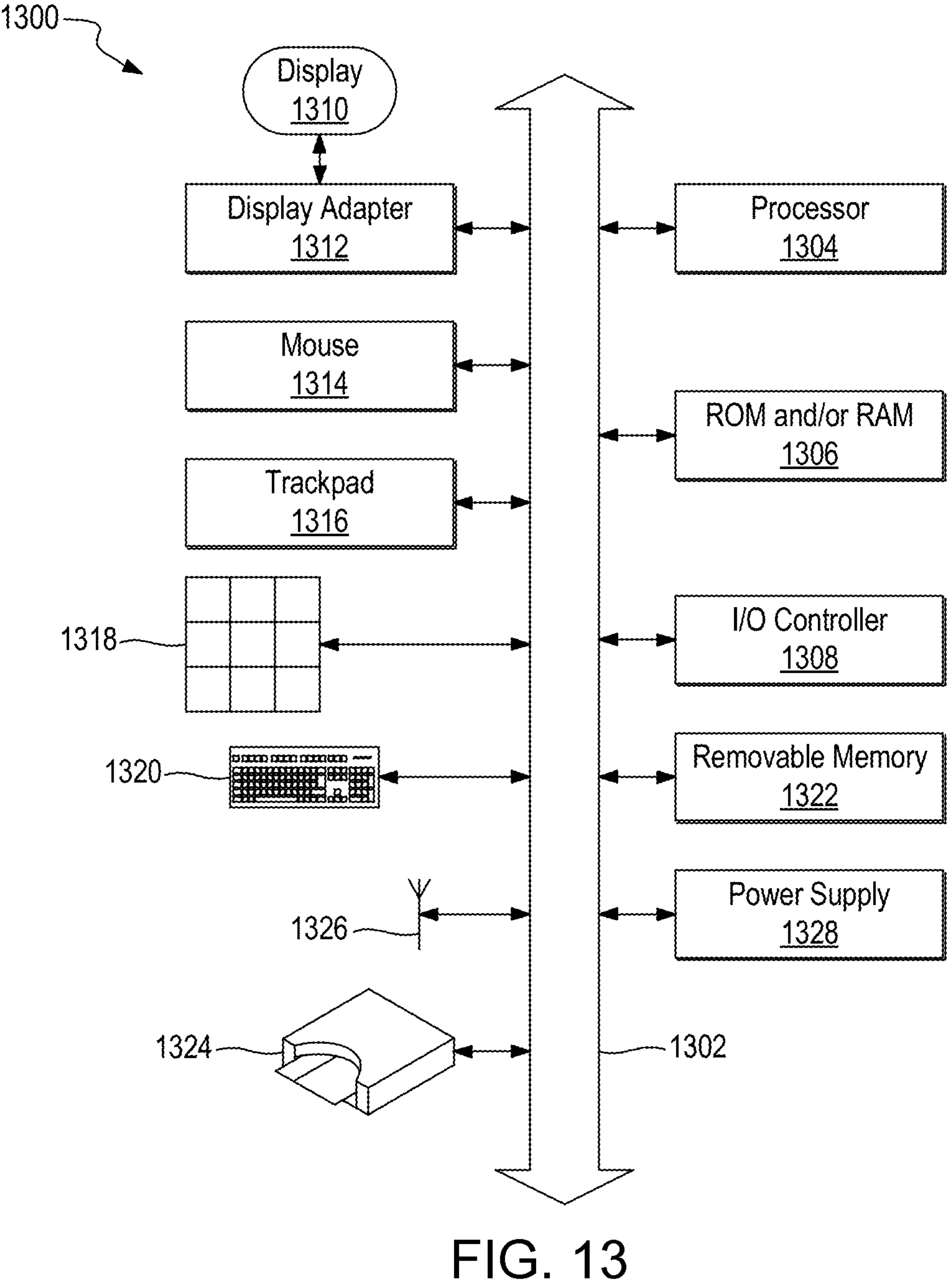
FIG. 13 illustrates an example system diagram of a computer system suitable for implementing aspects of an acute care predictive analytics tool and/or a tiered assessment tool.

FIG. 13 illustrates an example system diagram of a computer system 1300 suitable for implementing aspects of the predictive analytics tool and/or tiered assessment tool. System 1300 includes a bus 1302 which interconnects major subsystems such as a processor 1304, internal memory 1306 (such as RAM and/or ROM), an input/output (I/O) controller 1308, removable memory (such as a memory card) 1322, and external devices such as display screen 1310 via display adapter 1312, a mouse 1314, a trackpad 1316, a numeric keypad 1318, an alphanumeric keyboard 1320, a smart card adapter or acceptance device 1324, a wireless antennae or other interface 1326, and a power supply 1328. Many other devices can be connected. Wireless interface 1326 together with a wired network interface (not shown), may be used to interface to a local or wide area network (such as the Internet) using any network interface system known to those skilled in the art.

Many other devices or subsystems (not shown) may be connected in a similar manner (e.g., servers, personal computers, tablet computers, smart phones, mobile devices, etc.). Also, it is not necessary for all of the components depicted in FIG. 13 to be present to practice the presently disclosed technology. Furthermore, devices and components thereof may be interconnected in different ways from that shown in FIG. 13. Code to implement the presently disclosed technology may be operably disposed in the internal memory 1306 or stored on storage media such as the removable memory 1322, a thumb drive, a CompactFlash® storage device, a DVD-R ("Digital Versatile Disc" or "Digital Video Disc" recordable), a DVD-ROM ("Digital Versatile Disc" or "Digital Video Disc" read-only memory), a CD-R (Compact Disc-Recordable), or a CD-ROM (Compact Disc read-only memory). For example, in an implementation of the computer system 1300, code for implementing the predictive analytics tool/or a tiered assessment tool described in detail above may be stored in the internal memory 1306 and configured to be operated by the processor 1304.

Aspects of the acute care predictive analytics tool and/or a tiered assessment tool may be implemented in a tangible computer-readable storage media readable by a computer. The term "tangible computer-readable storage media" includes, but is not limited to, random access memory ("RAM"), read-only memory ("ROM"), electrically erasable programmable read-only memory ("EEPROM"), flash memory or other memory technology, compact disc read-only memory ("CD-ROM"), digital versatile disks (DVD) or other optical disk storage, magnetic cassettes, magnetic tape, magnetic disk storage or other magnetic storage devices, or any other tangible medium which can be used to store the desired information and which can be accessed by mobile device or computer. In contrast to tangible computer-readable storage media, intangible computer-readable communication signals may embody computer readable instructions, data structures, program modules, or other data resident in a modulated data signal, such as a carrier wave or other signal transport mechanism.

The above specification, examples, and data provide a complete description of the structure and use of exemplary embodiments of the invention. Since many embodiments of the invention can be made without departing from the spirit and scope of the invention, the invention resides in the claims hereinafter appended. Furthermore, structural features of the different embodiments may be combined in yet another embodiment without departing from the recited claims.

What is claimed is:

1. A computer-implemented method of providing tiered mobile health care services to a patient in the patient's home, the method being executed using a mobile computing device of a mobile acute care unit physically present at the patient's home, the method comprising:

displaying, on the mobile computing device, a user interface for the mobile acute care unit to enter patient identifying information, symptom information, and results of an initial acute care assessment of the patient;

performing an acute care service, including a short-term treatment for an injury, illness, or other urgent medical condition, on the patient in the patient's home by a mobile acute care unit physically present at the patient's home;

executing, using the mobile computing device, a threshold evaluation to determine patient eligibility for a specialized health care service to be rendered in the patient's home;

executing, using the mobile computing device, an environmental assessment of the patient's home by the same mobile acute care unit physically present at the patient's home, the environmental assessment including both patient-focused safety factors directed to safety of the patient in being rendered care in the patient's home and provider-focused safety factors directed to safety of a health-care provider in rendering a specialized health care service in the patient's home, wherein the provider-focused safety factors are posed to the mobile acute care unit via the user interface for the mobile computing device in the form of questions about the patient's home regarding potential risks to the health and safety of the health care provider rendering the specialized health care service in the patient's home, and wherein scores are assigned to the mobile acute care unit's responses to the questions;

executing, using the mobile computing device, a clinical assessment including a predefined set of tasks presented to the same mobile acute care unit via the user interface for the mobile computing device and performed by the same mobile acute care unit physically present at the patient's home, results of which are evaluated against predefined thresholds to assess the patient's condition, illness or injury;

computing a specialized care risk score based on the environmental assessment and the clinical assessment, the specialized care risk score attributable to providing the specialized health care service in the patient's home;

receiving via the mobile computing device, an approval for the patient to receive the specialized health care service in the patient's home at least based on a position of the specialized care risk score on a recommendation scale; and rendering the specialized health care service to treat the patient's condition, illness or injury by the health care provider in the patient's home.

2. The method of claim 1, wherein one or more of the patient-focused safety factors and the provider-focused safety factors are weighted, and where the weighting of one or more of the weighted patient-focused safety factors and the provider-focused safety factors changes based on the clinical assessment.

3. The method of claim 1, wherein the approval for the patient to receive the specialized health care service in the patient's home includes the mobile acute care unit conferring with a health care professional associated with the specialized health care service.

4. The method of claim 1, wherein the environmental assessment further includes social support factors for the patient.

5. The method of claim 1, wherein the clinical assessment is for providing one of hospital-level and long-term nursing care in the patient's home.

6. The method of claim 1, further comprising:

outputting a list of specialized equipment based on the environmental assessment and the clinical assessment for equipping the patient's home in advance of rendering the specialized health care service in the patient's home.

7. The method of claim 1, wherein the specialized health care service requires one or both of personnel and specialized equipment specific to the clinical assessment of the patient.

8. A computer-implemented method of providing specialized tiered mobile health care services to a patient in the patient's home, the method being executed using a mobile computing device of a mobile acute care unit physically present at the patient's home, the method comprising:

displaying, on the mobile computing device, a user interface for the mobile acute care unit to enter patient identifying information, symptom information, and results of an initial acute care assessment of the patient;

performing an acute care service, including a short-term treatment for an injury, illness, or other urgent medical condition, on the patient in the patient's home by a mobile acute care unit physically present at the patient's home;

executing, using the mobile computing device, a threshold evaluation to determine patient eligibility for in-home hospitalization;

executing, using the mobile computing device, an environmental assessment of the patient's home by the same mobile acute care unit physically present at the patient's home, the environmental assessment including both patient-focused safety factors directed to safety of the patient in being rendered care in the patient's home and provider-focused safety factors directed to safety of a health-care provider in rendering care in the patient's home, wherein the provider-focused safety factors are posed to the same mobile acute care unit via the user interface for the mobile computing device in the form of questions about the patient's home regarding potential risks to the health and safety of the health care provider rendering care in the patient's home, and wherein scores are assigned to the mobile acute care unit's responses to the questions;

executing, using the mobile computing device, a clinical assessment including a predefined set of tasks presented to the same mobile acute care unit via the user interface for the mobile computing device and performed by the same mobile acute care unit physically present at the patient's home, results of which are evaluated against predefined thresholds to assess the patient's condition, illness or injury;

computing a specialized care risk score based on the environmental assessment and the clinical assessment, the specialized care risk score attributable to risk in providing in-home hospitalization services to the patient;

receiving via the mobile computing device, an approval for the in-home hospitalization of the patient at least based on a position of the specialized care risk score on a recommendation scale; and rendering the in-home hospitalization services to treat the patient's condition, illness or injury in the patient's home.

9. The method of claim 8, wherein one or more of the patient-focused safety factors and the provider-focused safety factors are weighted, and where the weighting of one or more of the weighted patient-focused safety factors and the provider-focused safety factors changes based on the clinical assessment.

10. The method of claim 8, wherein the environmental assessment further includes social support factors for the patient.

11. The method of claim 8, further comprising:

outputting a list of specialized equipment based on the environmental assessment and the clinical assessment for equipping the patient's home in advance of rendering the in-home hospitalization of the patient.

12. The method of claim 8, further comprising:

presenting an indicator of risk in the form of the position of the specialized care risk score on the recommendation scale to the mobile acute care unit.

13. The method of claim 8, wherein the in-home hospitalization of the patient requires one or both of personnel and specialized equipment specific to the clinical assessment of the patient.

14. The method of claim 8, wherein the approval for the patient to receive the in-home hospitalization services includes the mobile acute care unit conferring with a health care professional associated with the in-home hospitalization services.

15. A computer-implemented method of providing tiered mobile health care services to a patient in the patient's home, the method being executed using a mobile computing device of a mobile acute care unit physically present at the patient's home, the method comprising:

displaying, on the mobile computing device, a user interface for the mobile acute care unit to enter patient identifying information, symptom information, and results of an initial acute care assessment of the patient;

performing an acute care service, including a short-term treatment for an injury, illness, or other urgent medical condition, on the patient in the patient's home by a mobile acute care unit physically present at the patient's home;

executing, using the mobile computing device, a threshold evaluation to determine patient eligibility for long-term nursing care in the patient's home;

executing, using the mobile computing device, an environmental assessment of the patient's home by the same mobile acute care unit physically present at the patient's home, the environmental assessment including both patient-focused safety factors directed to safety of the patient in being rendered long-term nursing care in the patient's home and provider-focused safety factors directed to safety of a health-care provider in rendering long-term nursing care in the patient's home, wherein the provider-focused safety factors are posed to the mobile acute care unit via the user interface for the mobile computing device in the form of questions about the patient's home regarding potential risks to the health and safety of the health care provider rendering long-term nursing care in the patient's home, and wherein scores are assigned to the mobile acute care unit's responses to the questions;

executing, using the mobile computing device, a clinical assessment including a predefined set of tasks presented to the same mobile acute care unit via the user interface for the mobile computing device and performed by the same mobile acute care unit physically present at the patient's home, results of which are evaluated against predefined thresholds to assess the patient's condition, illness or injury;

computing a specialized care risk score based on the environmental assessment and the clinical assessment, the specialized care risk score attributable to providing the long-term nursing care of the patient in the patient's home;

receiving via the mobile computing device, an approval for the long-term nursing care of the patient in the patient's home at least based on a position of the specialized care risk score on a recommendation scale; and rendering the long-term nursing care of the patient to treat the patient's condition, illness or injury in the patient's home.

16. The method of claim 15, wherein one or more of the patient-focused safety factors and the provider-focused safety factors are weighted, and where the weighting of one or more of the weighted patient-focused safety factors and the provider-focused safety factors changes based on the clinical assessment.

17. The method of claim 15, wherein the environmental assessment further includes social support factors for the patient.

18. The method of claim 15, further comprising:

outputting a list of specialized equipment based on the environmental assessment and the clinical assessment for equipping the patient's home in advance of rendering the long-term nursing care of the patient in the patient's home.

19. The method of claim 15, wherein the approval for the patient to receive the long-term nursing care in the patient's home includes the mobile acute care unit conferring with a health care professional associated with the long-term nursing care.

* * * * *